US012735676B2

(12) United States Patent
Isacoff et al.

(10) Patent No.: US 12,735,676 B2
(45) Date of Patent: Sep. 15, 2026

(54) AFFINITY-TAGGED PHOTOSWITCHES AND METHODS OF USE THEREOF

(71) Applicant: The Regents of the University of California, Oakland, CA (US)

(72) Inventors: Ehud Y. Isacoff, Berkeley, CA (US); Dirk Trauner, New York, NY (US); Johannes Broichhagen, Heidelberg (DE); Joshua Levitz, New York, NY (US)

(73) Assignee: The Regents of the University of California, Oakland, CA (US)

( * ) Notice: Subject to any disclaimer, the term of this patent is extended or adjusted under 35 U.S.C. 154(b) by 481 days.

(21) Appl. No.: 16/649,525

(22) PCT Filed: Sep. 21, 2018

(86) PCT No.: PCT/US2018/052307
§ 371 (c)(1),
(2) Date: Mar. 20, 2020

(87) PCT Pub. No.: WO2019/060785
PCT Pub. Date: Mar. 28, 2019

(65) Prior Publication Data

US 2020/0308539 A1 Oct. 1, 2020

Related U.S. Application Data

(60) Provisional application No. 62/561,882, filed on Sep. 22, 2017.

(51) Int. Cl.
*A61K 31/655* (2006.01)
*A61N 5/06* (2006.01)
(Continued)

(52) U.S. Cl.
CPC ........... *C12N 5/0621* (2013.01); *A61N 5/062* (2013.01); *C07K 14/705* (2013.01); *C07K 16/00* (2013.01);
(Continued)

(58) Field of Classification Search
CPC ..... C07K 14/705; C07K 14/36; C07K 14/195
See application file for complete search history.

(56) References Cited

U.S. PATENT DOCUMENTS

| | | | |
|---|---|---|---|
| 2007/0134665 A1 | 6/2007 | Dellaire et al. |
| 2015/0224193 A1 | 8/2015 | Isacoff et al. |
| 2016/0361437 A1 | 12/2016 | Lucas et al. |

FOREIGN PATENT DOCUMENTS

| | | |
|---|---|---|
| EP | 3146981 | 3/2017 |

OTHER PUBLICATIONS

Vafabakhsh et al., Conformational dynamics of a class C G-protein-coupled receptor. Nature 524, 497-501 (2015). https://doi.org/10.1038/nature14679 (Year: 2015).*

(Continued)

*Primary Examiner* — Aurora M Fontainhas
(74) *Attorney, Agent, or Firm* — Rudy J. Ng; Dana K. Lim; Bozicevic, Field & Francis LLP

(57) ABSTRACT

The present disclosure provides a conjugate comprising: a) an affinity agent that specifically binds a target ligand-binding polypeptide; and b) a photoisomerizable regulator comprising: i) a photoisomerizable moiety; and ii) a ligand that binds to the target ligand-binding polypeptide. The present disclosure provides cells comprising a conjugate of the present disclosure. The present disclosure provides methods of using a conjugate of the present disclosure to modulate activity of a target polypeptide, and to modulate activity of a target cell or cell population.

9 Claims, 6 Drawing Sheets

Specification includes a Sequence Listing.

(51) Int. Cl.
*C07K 14/705* (2006.01)
*C07K 16/00* (2006.01)
*C12N 5/077* (2010.01)
*C12N 5/079* (2010.01)
*C12N 5/0793* (2010.01)
*A61K 38/00* (2006.01)

(52) U.S. Cl.
CPC ......... *C12N 5/0619* (2013.01); *C12N 5/0652* (2013.01); *A61K 38/00* (2013.01); *C07K 2317/569* (2013.01); *C07K 2317/622* (2013.01); *C07K 2319/20* (2013.01); *C12N 2529/10* (2013.01)

(56) References Cited

OTHER PUBLICATIONS

AlmagroJC, FranssonJ. Humanization of antibodies. FrontBiosci. Jan. 1, 2008; 13: 1619-33. (Year: 2008).*

Edwards et al. The remarkable flexibility of the human antibody repertoire isolation of over one thousand different antibodies to a single protein, BLyS. JMolBiol Nov. 14, 2003;334(1): 103-18. (Year: 2003).*

Single-domain antibody (sdAb); Wikipedia , downloaded Nov. 17, 2025; https://en.wikipedia.org/wiki/Single-domain_antibody (Year: 2025).*

Farrants, et al.; "SNAP-tagged nanobodies enable reversible optical control of a G protein-coupled receptor via a remotely tethered photoswitchable ligand"; bioRxiv; XP055800072, DOI: 10.1101/266247, Retrieved from the Internet: URL:https://www.biorxiv.org/content/10.110_1/266247vl.full.pdi; 18 pages (Feb. 15, 2018).

Barber, et al.; "Optical control of AMPA receptors using a photoswitchable quinoxaline-2,3-dione antagonist"; Chemical Science; vol. 8, pp. 611-615 (2017).

Broichhagen, et al.; "Orthogonal Optical Control of a G Protein-Coupled Receptor with a SNAP-Tethered Photochromic Ligand"; ACS Central Science; vol. 1, pp. 383-393 (2015).

England, et al.; "HaloTag Technology: A Versatile Platform for Biomedical Applications"; Bioconjugate Chemistry; vol. 26, pp. 975-986 (2015).

Komaromy, et al.; "Targeting Gene Expression to Cones with Human Cone Opsin Promoters in Recombinant AAV"; Gene. Ther.; vol. 15, No. 14, pp. 1049-1055 (Jul. 2008).

Lemoine, et al.; "Optical control of an ion channel gate"; PNAS; vol. 110, No. 51, pp. 20813-20818 (Dec. 17, 2013).

Schmidt, et al; "A fully genetically encoded protein architecture for optical control of peptide ligand concentration"; Nature Communications; vol. 5, No. 2019, pp. 1-8 (Jan. 10, 2014).

Schultz, et al.; "Simultaneous Protein Tagging in Two Colors"; Chemistry & Biology; vol. 15, pp. 91-92 (Feb. 2008).

Shields, et al.; "Deconstructing behavioral neuropharmacology with cellular specificity"; Science; vol. 356, pp. 1-9 (Apr. 7, 2017).

Stagge, et al.; "Snap-, CLIP- and Halo-Tag Labelling of Budding Yeast Cells"; PLoS One; vol. 8, No. 10, pp. 1-9 (Oct. 2013).

Tochitsky, et al.; "Optochemical control of genetically engineered neuronal nicotinic acetylcholine receptors"; Nat. Chem.; vol. 4, No. 2, pp. 105-111 (Aug. 8, 2016).

* cited by examiner

FIG. 1 Schematic showing two established photoswitch attachment strategies and exemplary "gene-free" immunochemistry strategy.

FIG. 2. Optical control of GFP-mGluR2 via Photoswitch Conjugation to a SNAP-tagged anti-GFP Nanobody (NB).

FIG. 3. Optical control of GFP-mGluR2 via co-expression of SNAP-tagged anti-GFP NBs.

FIG. 4. Nanobody attachment to GFP-mGluR2 does not alter glutamate response.

Nanobody NB-8260 binding to mGluR5 ectodomain (in absence of glutamate) activates the receptor and triggers calcium waves in HEK293 cells.

A
anti-mGluR5 ab
Biotinylated secondary ab
PEG-biotin
Human_mGluR5
neutravidin
PEG
B
Active
Inactive
Count
FRET
0 glu + NB
0.8 uM glu + NB
0 glu
0.8 uM glu
C
NB-8236
NB-8243
NB-8260
Count
FRET

AFFINITY-TAGGED PHOTOSWITCHES AND METHODS OF USE THEREOF

CROSS-REFERENCE

This application is a national phase filing under 35 U.S.C. § 371 of PCT/US2018/052307, filed Sep. 21, 2018, which claims the benefit of U.S. Provisional Patent Application No. 62/561,882, filed Sep. 22, 2017, which applications are incorporated herein by reference in their entirety.

STATEMENT REGARDING FEDERALLY SPONSORED RESEARCH

This invention was made with government support under Grant No. EY018241 awarded by the National Institutes of Health. The government has certain rights in the invention.

SEQUENCE LISTING

The Sequence Listing TXT file, "BERK-362WO SEQ LISTING 20260422_ST25," created on Apr. 22, 2026, and having a size of 7,680 bytes, is hereby incorporated by reference.

INTRODUCTION

Photochromic molecules have emerged as powerful optical tools to control protein and cellular function in neuroscience. Photoswitching changes the geometry of the tether on a ligand to alter the ligand's effective concentration at its binding site or its ability to bind, thereby modulating protein function.

SUMMARY

The present disclosure provides a conjugate comprising: a) an affinity agent that specifically binds a target ligand-binding polypeptide; b) a photoisomerizable regulator comprising: i) a photoisomerizable moiety; and ii) a ligand that binds to the target ligand-binding polypeptide; and c) a linker that connects (a) and (b). The present disclosure provides cells comprising a conjugate of the present disclosure. The present disclosure provides methods of using a conjugate of the present disclosure to modulate activity of a target polypeptide, and to modulate activity of a target cell or cell population.

BRIEF DESCRIPTION OF THE DRAWINGS

FIG. 1D depicts an exemplary embodiment, using immunochemistry with a nanobody; for example, a photoswitch is delivered to a target protein mGluR2 using a nanobody specific for an epitope on the target protein. The photoswitch is coupled to the nanobody using a tagging moiety such as SNAP.

DEFINITIONS

Figure 1:
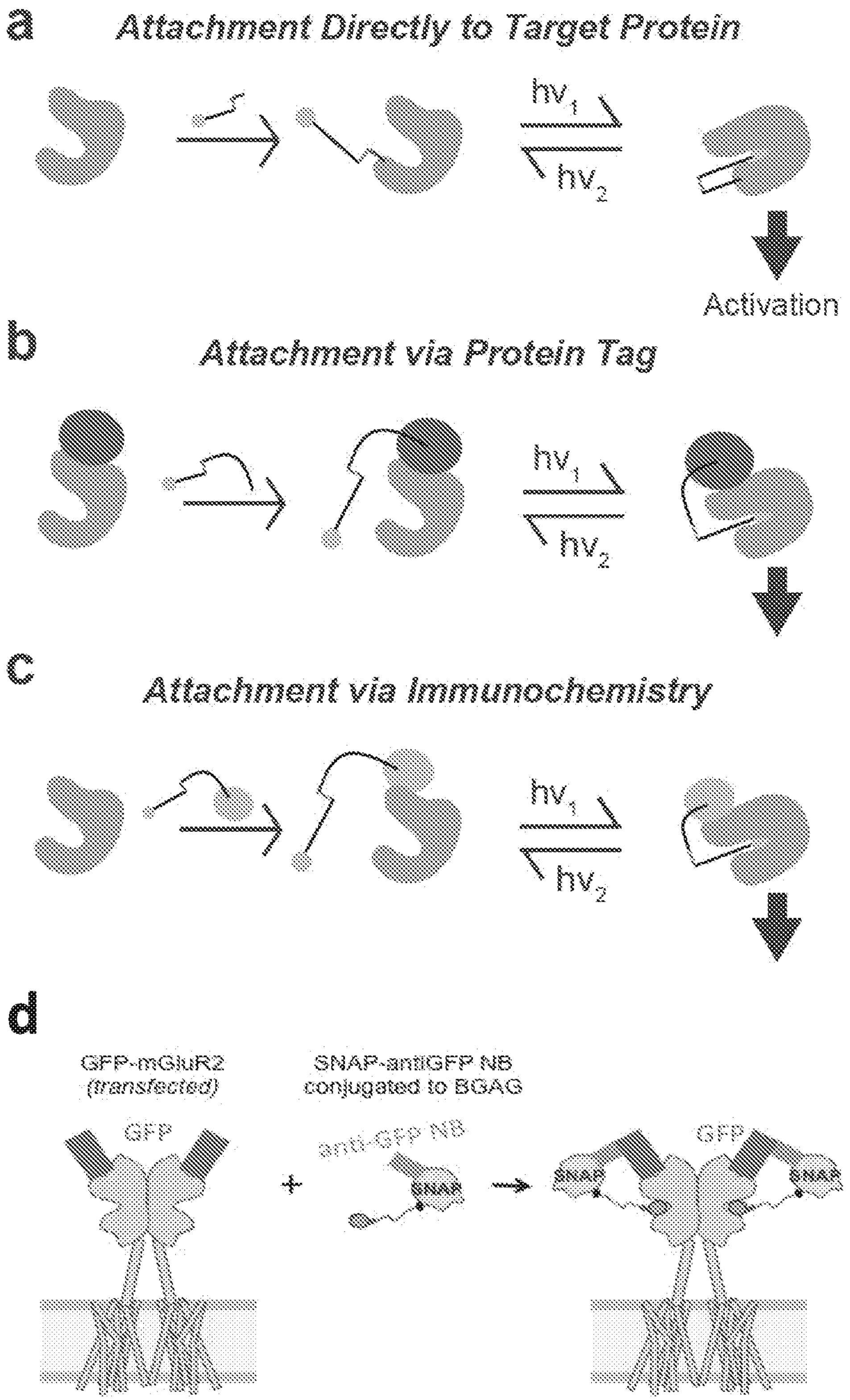
FIG. 1A-1D compare two photoswitch attachment strategies (a) and (b) to exemplary embodiments of the present disclosure (c). a,b). In the methods depicted in (a) and (b), the photoswitch is attached covalently either directly to the target protein, e.g. by a maleimide conjugation to a cysteine introduced into the target protein (a), or indirectly, via an enzymatic domain, such as SNAP or CLIP or HALO, which is genetically fused to the target protein (b). c) In exemplary embodiments of the present disclosure, an affinity domain, which binds the target protein selectively, is pre-conjugated to the photoswitch and delivers it to the target protein.

The following terms have the following meanings unless otherwise indicated. Any undefined terms have their art recognized meanings.

The term "alkyl" refers to a monoradical branched or unbranched saturated hydrocarbon chain, e.g., having from 1 to 40 carbon atoms, from 1 to 10 carbon atoms, or from 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above wherein one or more carbon atoms in the alkyl chain have been optionally replaced with a heteroatom such as —O—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —$SO_2$-alkyl, —$SO_2$-aryl, —$SO_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "alkylaminoalkyl", "alkylaminoalkenyl" and "alkylaminoalkynyl" refers to the groups $R^aNHR^b$— where $R^a$ is alkyl group as defined above and $R^b$ is alkylene, alkenylene or alkynylene group as defined above.

The term "alkaryl" or "aralkyl" refers to the groups -alkylene-aryl and -substituted alkylene-aryl where alkylene, substituted alkylene and aryl are defined herein.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

The term "alkenyl" refers to a monoradical of a branched or unbranched unsaturated hydrocarbon group having from 2 to 40 carbon atoms, from 2 to 10 carbon atoms, or from 2 to 6 carbon atoms and having at least 1 site (e.g., from 1-6 sites) of vinyl unsaturation.

The term "substituted alkenyl" refers to an alkenyl group as defined above having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "alkynyl" refers to a monoradical of an unsaturated hydrocarbon having from 2 to 40 carbon atoms, from 2 to 20 carbon atoms, or from 2 to 6 carbon atoms and having at least 1 site (e.g., from 1-6 sites) of acetylene (triple bond) unsaturation.

The term "substituted alkynyl" refers to an alkynyl group as defined above having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, and —$SO_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl, and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl, and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl, and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl, and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl).

Exemplary aryls include phenyl, naphthyl and the like. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

The term "aryloxy" refers to the group aryl-O— wherein the aryl group is as defined above including optionally substituted aryl groups as also defined herein.

The term "amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclic provided that both R's are not hydrogen.

The term "carboxyalkyl" or "alkoxycarbonyl" refers to the groups "—C(O)O-alkyl", "—C(O)O— substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl, and the like.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring). Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$— alkyl, —$SO_2$-substituted alkyl, —$SO_2$-aryl and —$SO_2$-heteroaryl, and trihalomethyl.

The term "heteroaralkyl" refers to the groups -alkylene-heteroaryl where alkylene and heteroaryl are defined herein. Such heteroaralkyl groups are exemplified by pyridylmethyl, pyridylethyl, indolylmethyl, and the like.

The term "heteroaryloxy" refers to the group heteroaryl-O—.

The term "heterocycle" or "heterocyclic" refers to a monoradical saturated or unsaturated group having a single ring or multiple condensed rings, from 1 to 40 carbon atoms and from 1 to 10 hetero atoms, e.g., from 1 to 4 heteroatoms, selected from nitrogen, sulfur, phosphorus, and/or oxygen within the ring. Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

Examples of nitrogen heteroaryls and heterocycles include, but are not limited to, pyrrole, thiophene, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, pyrrolidine, piperidine, piperazine, indoline, morpholine, tetrahydrofuranyl, tetrahydrothiophene, and the like as well as N-alkoxy-nitrogen containing heterocycles.

The term "heterocyclooxy" refers to the group heterocyclic-O—.

The term "heterocyclothio" refers to the group heterocyclic-S—.

The term "heterocyclene" refers to the diradical group formed from a heterocycle, as defined herein, and is exemplified by the groups 2,6-morpholino, 2,5-morpholino and the like.

The term "heteroarylamino" refers to a 5 membered aromatic ring wherein one or two ring atoms are N, the remaining ring atoms being C. The heteroarylamino ring may be fused to a cycloalkyl, aryl or heteroaryl ring, and it may be optionally substituted with one or more substituents, e.g., one or two substituents, selected from alkyl, substituted alkyl, cycloalkyl, aryl, aralkyl, heteroaryl, heteroaralkyl, halo, cyano, acyl, amino, substituted amino, acylamino, —OR (where R is hydrogen, alkyl, alkenyl, cycloalkyl, acyl, aryl, heteroaryl, aralkyl, or heteroaralkyl), or —$S(O)_nR$ where n is an integer from 0 to 2 and R is hydrogen (provided that n is 0), alkyl, alkenyl, cycloalkyl, amino, heterocyclo, aryl, heteroaryl, aralkyl, or heteroaralkyl.

The term "heterocycloamino" refers to a saturated monovalent cyclic group of 4 to 8 ring atoms, wherein at least one ring atom is N and optionally contains one or two additional ring heteroatoms selected from the group consisting of N, O, or S(O)n (where n is an integer from 0 to 2), the remaining ring atoms being C, where one or two C atoms may optionally be replaced by a carbonyl group. The heterocycloamino ring may be fused to a cycloalkyl, aryl or heteroaryl ring, and it may be optionally substituted with one or more substituents, e.g., one or two substituents, selected from alkyl, substituted alkyl, cycloalkyl, aryl, aralkyl, heteroaryl, heteroaralkyl, halo, cyano, acyl, amino, substituted amino, acylamino, —OR (where R is hydrogen, alkyl, alkenyl, cycloalkyl, acyl, aryl, heteroaryl, aralkyl, or heteroaralkyl), or —S(O)$_n$R [where n is an integer from 0 to 2 and R is hydrogen (provided that n is 0), alkyl, alkenyl, cycloalkyl, amino, heterocyclo, aryl, heteroaryl, aralkyl, or heteroaralkyl].

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" or "alkylthio" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of the embodiments include all stereochemical isomers arising from the substitution of these compounds.

The term "pharmaceutically-acceptable salt" refers to salts which retain biological effectiveness and are not biologically or otherwise undesirable. In many cases, the compounds of the embodiments are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component.

A polypeptide has a certain percent "sequence identity" to another polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wisconsin, USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;

Gap Penalty: 1.00;

Gap Size Penalty: 0.33; and

Joining Penalty: 30.0.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses, camels, etc.); mammalian farm animals (e.g., sheep, goats, cows, etc.); mammalian pets (dogs, cats, etc.); and rodents (e.g., mice, rats, etc.). In some cases, the individual is a human.

The term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. In some cases, the linker backbone includes a linking functional group, such as an ether, thioether, amino, amide, sulfonamide, carbamate, thiocarbamate, urea, thiourea, ester, thioester or imine. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (iso-propyl), nbutyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The terms "polyethylene oxide", "PEO", "polyethylene glycol" and "PEG" are used interchangeably and refer to a polymeric group including a chain described by the formula $-(CH_2-CH_2-O-)_n-$ or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a conjugate" includes a plurality of such conjugates and reference to "the photoisomerizable moiety" includes reference to one or more photoisomerizable moieties and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a conjugate comprising: a) an affinity agent that specifically binds a target ligand-binding polypeptide; b) a photoisomerizable regulator comprising: i) a photoisomerizable moiety; and ii) a ligand that binds to the target ligand-binding polypeptide; and c) a linker that connects (a) and (b). The present disclosure provides cells comprising a conjugate of the present disclosure. The present disclosure provides methods of using a conjugate of the present disclosure to modulate activity of a target polypeptide, and to modulate activity of a target cell or cell population.

Affinity-Tagged Photoswitches

The present disclosure provides a conjugate comprising: a) an affinity agent that specifically binds a target ligand-binding polypeptide; b) a photoisomerizable regulator comprising: i) a photoisomerizable moiety; and ii) a ligand that binds to the target ligand-binding polypeptide; and c) a linker that connects (a) and (b). A conjugate of the present disclosure is also referred to herein as an "affinity-tagged photoswitch." A photoisomerizable regulator is also referred to herein as a "photoswitch."

A conjugate of the present disclosure modulates activity of a target ligand-binding polypeptide. The photoisomerizable regulator interacts with the target ligand-binding polypeptide, and the ligand present in the photoisomerizable regulator binds to a ligand-binding site in the target ligand-binding polypeptide in a manner that is controlled by light. Depending on factors such as the ligand, the design of the photoisomerizable regulator, and the wavelength of light, a conjugate of the present disclosure can increase or decrease activity of the target ligand-binding polypeptide, can modulate (increase or decrease) its sensitivity to other stimuli, can stabilize the target ligand-binding polypeptide in a particular conformation, or can induce a conformational change in the target ligand-binding polypeptide.

The affinity agent present in a conjugate of the present disclosure binds to a target ligand-binding polypeptide, and thereby brings the ligand present in the conjugate into proximity with the target ligand-binding polypeptide such that the ligand can bind, in a light-dependent manner, to a ligand-binding site in the target ligand-binding polypeptide. When a conjugate of the present disclosure binds to a target ligand-binding polypeptide, the target ligand-binding polypeptide becomes a light-regulated polypeptide.

A change in the wavelength and/or intensity of light ($\Delta\lambda$) to which the light-regulated polypeptide is exposed results in a change in ligand binding to a ligand-binding site of the light-regulated polypeptide, e.g., results in a change in binding of the ligand portion of a conjugate of the present disclosure to the ligand-binding site of the light-regulated polypeptide. A "change in the wavelength of light to which the light-regulated polypeptide is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. Repetitive changing from $\lambda_1$ to $\lambda_2$, then from $\lambda_2$ to $\lambda_1$, and back, e.g., switching from a first wavelength to a second wavelength, and back again repeatedly, is also contemplated. Repetitive changing from light to darkness, from darkness to light, etc., is also contemplated.

In some cases, the change in wavelength (from $\lambda_1$ to $\lambda_2$; from light to darkness; or from darkness to light) results in a change in binding of the ligand to a ligand-binding site. As used herein, a "change in binding of a ligand to a ligand-binding site" includes increased binding and decreased binding. As used herein, "increased binding" includes one or more of: an increased probability of binding of the ligand to the ligand-binding site; an increased binding affinity of the ligand for the ligand-binding site; an increased local concentration of the ligand at the ligand-binding site; and an increased occupancy of the ligand in the ligand-binding site. As used herein, "decreased binding" includes one or more of: a decreased probability of binding of the ligand to the ligand-binding site; a decreased binding affinity of the ligand for the ligand-binding site; a decreased local concentration of the ligand at the ligand-binding site; and a decreased occupancy of the ligand in the ligand-binding site. As used herein, the term "change in wavelength" to which a conjugate of the present disclosure regulator is exposed, or to which a receptor/synthetic light regulator complex is exposed, refers to a change in wavelength from $\lambda_1$ to $\lambda_2$; a change from light to darkness; or a change from darkness to light. An increase in binding includes an increase of from about 10% to about 20%, from about 20% to about 50%, from about 50% to about 2-fold, from about 2-fold to about 5-fold, from about 5-fold to about 10-fold, from about 10-fold to about 50-fold, from about 50-fold to about $10^2$-fold, from about $10^2$-fold to about $10^4$-fold, from about $10^4$-fold to about $10^6$-fold, from about $10^6$-fold to about $10^8$-fold, or a greater than $10^8$-fold increase in binding. A decrease in binding includes a decrease of from about 5% to about 10% to about 20% to about 30%, from about 30% to about 40%, from about 40% to about 50%, from about 50% to about 60%, from about 60% to about 70%, from about 70% to about 80%, from about 80% to about 90%, or from about 90% to 100% decrease in binding.

For example, in some cases, the ligand has a first probability of binding to the ligand site at a first wavelength of light; the ligand has a second probability of binding to the ligand binding site at a second wavelength of light; and the second probability is lower than the first probability. In other cases, the ligand has a first probability of binding to the ligand site at a first wavelength of light; the ligand has a second probability of binding to the ligand binding site at a second wavelength of light; and the second probability is higher than the first probability. In other cases, ligand has a first probability of binding to the ligand site when exposed to light; the ligand has a second probability of binding to the ligand binding site in the absence of light (e.g., in darkness); and the second probability is lower than the first probability. In other cases, the ligand has a first probability of binding to the ligand site when exposed to light; the ligand has a second probability of binding to the ligand binding site in the absence of light and the second probability is higher than the first probability.

The local concentration of the ligand portion of a conjugate of the present at the ligand binding site in a light-regulated polypeptide is high. For example, the local concentration of the ligand portion of a conjugate of the present disclosure at the ligand binding site in a subject light-regulated polypeptide ranges from about 500 nM to about 50 mM, e.g., from about 500 nM to about 750 nM, from about 750 nM to about 1 mM, from about 1 mM to about 5 mM, from about 5 mM to about 10 mM, from about 10 mM to about 20 mM, from about 20 mM to about 30 mM, or from about 30 mM to about 50 mM.

Change in Wavelength Resulting in Binding of the Ligand to the Ligand-Binding Site or Higher Affinity Ligand Binding to Ligand-Binding Site In some cases, a change in the wavelength of light to which a light-regulated polypeptide is exposed results in an increase in binding affinity of the ligand portion of a conjugate of the present disclosure for a ligand-binding site the light-regulated polypeptide. For example, in some cases, a change in wavelength of light to which a light-regulated polypeptide is exposed results in an at least about 10%, at least about 20%, at least about 30%, at least about 50%, at least about 75%, at least about 2-fold, at least about 5-fold, at least about 10-fold, at least about 25-fold, at least about 50-fold, at least about 100-fold, at least about 250-fold, at least about 500-fold, at least about $10^3$-fold, at least about $5\times10^3$-fold, at least about $10^4$-fold, at least about $5\times10^4$-fold, or greater, increase in binding affinity.

Where the ligand is an agonist, the change in wavelength will in some cases result in activation of a light-regulated polypeptide. Where the ligand is an agonist, the change in wavelength will in some cases result in desensitization of a light-regulated polypeptide. Conversely, where the ligand is an antagonist, the change in wavelength results in a block of activation of a light-regulated polypeptide, e.g., block of the ability to activate a light-regulated polypeptide with free agonist. Where the ligand is a blocker (e.g., a pore blocker of an ion channel, or an interaction domain that binds to other biological macromolecules such as polypeptides or nucleic acids), the change in wavelength results in block of polypeptide activity.

Expressed another way, where the ligand is an agonist, and where a change in the wavelength of light to which a light-regulated polypeptide is exposed results in a higher binding affinity of the ligand moiety of the conjugate to the ligand-binding site of the light-regulated polypeptide, the change in wavelength results in transition from an inactive state to an active state, or to a desensitized state. Where the ligand is an antagonist, the change in wavelength results in transition from a responsive state to an unresponsive state. Where the ligand is a blocker, the change in wavelength results in transition from an active state to an inactive state.

Change in Wavelength Resulting in Removal of Ligand from Ligand-Binding Site, or Reduced Binding Affinity In some cases, a change in the wavelength of light to which a light-regulated polypeptide is exposed results in removal of the ligand portion of a conjugate of the present disclosure from a ligand-binding site of the light-regulated polypeptide, e.g., the ligand is not bound to the ligand-binding site. In some cases, a change in the wavelength of light to which the light-regulated polypeptide is exposed results in reduced binding affinity of the ligand portion of conjugate of the present disclosure for a ligand-binding site of the light-regulated polypeptide, e.g., the ligand has reduced binding affinity for the ligand-binding site. For example, in some cases, a change in the wavelength of light to which a light-regulated polypeptide is exposed results in a reduction of binding affinity of at least about 10%, at least about 20%, at least about 25%, at least about 30%, at least about 40%, at least about 50%, at least about 60%, at least about 70%, at least about 80%, at least about 90%, at least about 95%, or more.

Where the ligand is an agonist, the change in wavelength will in some cases result in activation of a light-regulated polypeptide. Where the ligand is an agonist, the change in wavelength will in some cases result in deactivation of a light-regulated polypeptide. Where the ligand is an agonist, the change in wavelength will in some cases result in recovery from desensitization of the light-regulated polypeptide. Conversely, where the ligand is an antagonist, the change in wavelength will in some cases result in occupancy of the ligand binding site and a reduction in background activity of the polypeptide, or, alternatively, in loss of activation by physiological stimuli. Where the ligand is an antagonist, the change in wavelength will in some cases result in removal of antagonism to permit activation by physiological stimuli. Where the ligand is a negative allosteric modulator, the change in wavelength that causes binding can result in increased sensitivity to or efficacy of another stimulus. Where the ligand is a positive allosteric modulator, the change in wavelength that causes binding can result in decreased sensitivity to or efficacy of another stimulus. In some cases, the ligand binding site will be a modulatory site where binding by the ligand increases or decreases the sensitivity to or efficacy of another stimulus, so that light regulates this process by controlling the binding of the photoswitched regulator. In some cases, the ligand is a blocker of an active site of the polypeptide (e.g., a pore blocker of an ion channel, or an interaction domain that binds to other biological macromolecules such as polypeptides or nucleic acids, or a blocker of an enzyme active site), and the change in wavelength results in block or relief of block in polypeptide activity to prevent or permit the receptor to function normally.

Expressed another way, where the ligand is an agonist, and where a change in the wavelength of light to which the light-regulated polypeptide is exposed results in removal (or non-binding) of the ligand moiety of conjugate of the present disclosure from the ligand-binding site of the light-regulated polypeptide, the change in wavelength results in transition from a more active state to a less active state, or from a desensitized state to a responsive state. Where the ligand is a negative allosteric modulator, the change in wavelength that causes un-binding results in increased sensitivity to or efficacy of another stimulus. Where the ligand is a positive allosteric modulator, the change in wavelength that causes un-binding results in decreased sensitivity to or efficacy of another stimulus. Where the ligand is an antagonist, the change in wavelength that causes un-binding results in transition from an unresponsive state to a responsive state or from an inactive state to a state with some background "basal" (unliganded) activity. Where the ligand is a blocker, the change in wavelength that causes un-binding results in transition from an inactive state to an active state.

Affinity Agents

The affinity agent targets the photoisomerizable regulator to a target ligand-binding polypeptide. In some cases, the affinity agent binds specifically to a target ligand-binding polypeptide. Thus, for example, in some cases, the affinity agent binds to a target ligand-binding polypeptide with an affinity of at least $10^{-6}$ M, at least $10^{-7}$ M, at least $10^{-8}$ M, at least $10^{-9}$ M, or at least $10^{-10}$ M.

Suitable affinity agents include, but are not limited to, small molecules, RNA aptamers, DNA aptamers, peptides, and antibodies. Suitable affinity agents include affinity agents identified by phase display.

Antibodies

In some cases, an affinity agent present in a conjugate of the present disclosure is an antibody. An antibody suitable for inclusion in a conjugate of the present disclosure binds to a target ligand-binding polypeptide. Examples of target ligand-binding polypeptide are provided below. An antibody suitable for inclusion in a conjugate of the present disclosure does not inhibit binding of the ligand present in the photoisomerizable regulator to the target ligand-binding polypeptide. Generally, an antibody suitable for inclusion in a conjugate of the present disclosure does not substantially alter activity of the target ligand-binding polypeptide.

The terms "antibodies" and "immunoglobulin" include antibodies or immunoglobulins of any isotype, fragments of antibodies that retain specific binding to antigen (e.g., to a target ligand-binding polypeptide), including, but not limited to, Fab, Fv, scFv, and Fd fragments, chimeric antibodies, humanized antibodies, single-chain antibodies (scAb), single domain antibodies (sdAb), single domain heavy chain antibodies, a single domain light chain antibodies, nanobodies, bi-specific antibodies, multi-specific antibodies, and fusion proteins comprising an antigen-binding (also referred to herein as antigen binding) portion of an antibody and a non-antibody protein. Also encompassed by the term are Fab', Fv, $F(ab')_2$, and or other antibody fragments that retain specific binding to antigen, and monoclonal antibodies.

The term "nanobody" (Nb), as used herein, refers to the smallest antigen binding fragment or single variable domain ($V_{HH}$) derived from naturally occurring heavy chain antibody and is known to the person skilled in the art. They are derived from heavy chain only antibodies, seen in camelids. In the family of "camelids" immunoglobulins devoid of light polypeptide chains are found. "Camelids" comprise old world camelids (*Camelus bactrianus* and *Camelus dromedarius*) and new world camelids (for example, Llama *paccos, Llama glama, Llama guanicoe* and Llama *vicugna*). A single variable domain heavy chain antibody is referred to herein as a nanobody or a $V_{HH}$ antibody.

Cartilaginous fishes also have heavy-chain antibodies (IgNAR; "immunoglobulin new antigen receptor"), from which single-domain antibodies called $V_{NAR}$ fragments can be obtained. Thus, in some cases, an affinity agent is an IgNAR.

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al. (1995) *Protein Eng.* 8(10): 1057-1062); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen. Antibody fragments include, e.g., scFv, sdAb, dAb, Fab, Fab', $Fab'_2$, $F(ab')_2$, Fd, Fv, Feb, and SMIP. Examples of sdAb are a camelid VHH and a cartilaginous fish VNAR.

"Fv" is the minimum antibody fragment that contains a complete antigen-recognition and -binding site. This region consists of a dimer of one heavy- and one light-chain variable domain in tight, non-covalent association. It is in this configuration that the three complementarity determining regions (CDRs) of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

An antibody suitable for inclusion in a conjugate of the present disclosure can be a fusion polypeptide, e.g., a fusion polypeptide comprising: i) an antibody that binds a target polypeptide; and ii) a fusion partner. In some cases, the fusion partner is an anchoring domain that provides for covalent attachment of a photoisomerizable regulator, either directly or via a linker. In some cases, the fusion partner is a HALO tag. In some cases, the fusion partner is a CLIP tag. In some cases, the fusion partner is a SNAP tag.

Small Molecules

Small molecules that are suitable for use as affinity agent in a conjugate of the present disclosure include small molecules having a molecular weight of less than 2 kDa, less than 1 kDa, less than 500 Daltons, less than 250 Daltons, less than 200 Daltons, less than 100 Daltons, less than 75 Daltons, or less than 50 Daltons. For example, a small molecule that is suitable for use as affinity agent in a conjugate of the present disclosure can have a molecular weight of from 10 Daltons to 2 kDa, e.g., from 10 Daltons to 25 Daltons, from 25 Daltons to 50 Daltons, from 50 Daltons to 100 Daltons, from 100 Daltons to 150 Daltons, from 150 Daltons to 250 Daltons, from 250 Daltons to 500 Daltons, from 500 Daltons to 1 kDa, or from 1 kDa to 2 kDa.

A small molecule that is suitable for use as affinity agent in a conjugate of the present disclosure is generally not a ligand for a target ligand-binding polypeptide. A small molecule that is suitable for use as affinity agent in a conjugate of the present disclosure generally binds to the target ligand-binding polypeptide at a site other than the site at which the ligand binds, and does not substantially inhibit binding of the ligand to the target ligand-binding polypeptide.

Aptamers

Aptamers that are suitable for use as affinity agent include RNA aptamers, DNA aptamers, and peptide aptamers. An aptamer suitable for inclusion in a conjugate of the present disclosure does not inhibit binding of the ligand present in the photoisomerizable regulator to the target ligand-binding polypeptide. Generally, an aptamer suitable for inclusion in a conjugate of the present disclosure does not substantially alter activity of the target ligand-binding polypeptide.

Nucleic acid aptamers can have a length of from about 10 nucleotides to about 200 nucleotides, e.g., from 10 nucleotides (nt) to 15 nt, from 10 nt to 15 nt, from 15 nt to 20 nt, from 20 nt to 25 nt, from 25 nt to 50 nt, from 50 nt to 75 nt, form 75 nt to 100 nt, from 100 nt to 150 nt, or from 150 nt to 200 nt. Nucleic acid aptamers can have a length of from about 10 nucleotides to about 50 nucleotides. Nucleic acid aptamers can have a length of from about 10 nucleotides to about 25 nucleotides.

A DNA aptamer can be prepared using any known method. For example, a DNA-SELEX method can be used. In the SELEX method, by setting strict selection conditions by increasing the number of rounds or using a competing substance, an aptamer exhibiting a stronger binding potential for a target polypeptide is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained. The SELEX method comprises a process of amplification by polymerase chain reaction; by causing a mutation by using manganese ions and the like in the process, it is possible to perform SELEX with higher diversity. Aptamers specific for a polypeptide (or portion of a polypeptide) can be produced using standard techniques, such as, for example, those described in Ogawa, A., et al., Bioorg. Med. Chem, Lett, 14: 4001-4004, 2004; and Jayasena, S. D., Clinical Chemistry 45: 1628-1650, 1999.

A nucleic acid aptamer can include naturally-occurring nucleotides, and may also include non-naturally-occurring nucleotides. DNA aptamers that include only naturally-occurring nucleotides include DNA aptamers composed of deoxyribonucleotides having any of the natural bases adenine, guanine, cytosine, and thymine. RNA aptamers that include only naturally-occurring nucleotides include RNA aptamers composed of RNAs composed of ribonucleotides having any of the natural bases adenine, guanine, cytosine, and uracil. A non-naturally-occurring nucleotide comprises a non-naturally occurring base, a phosphate group, and a sugar. A non-naturally-occurring base (or "artificial base") refers to an artificially constructed base analog having properties similar to those of the natural base constituting the natural nucleotide and that can form artificial base pairing with its partner base analog (referred to as a "complementary artificial base"), as in the natural base. The term "artificial base pairing" refers to base pairing formed between a pair of complementary artificial bases, as in a pair of complementary natural bases adenine and thymine, adenine and uracil, or guanine and cytosine. Artificial base pairing includes a chemical bond via a hydrogen bond found in the base pairing between natural bases, a physical bond via the molecular structure-based association between artificial bases, and stacking effects via hydrophobic interaction.

Aptamers can be modified to comprise one or more moieties such as: a 2'-O-methyl moiety; a 2'-$NH_2$ moiety; and the like.

Aptamers that bind a variety of polypeptides are known in the art. For example, an aptamer database is available on the internet at aptagen(dot)com/aptamer-index/aptamer-list. In addition, as noted above, those skilled in the art can readily design aptamers that bind a target ligand-binding polypeptide of interest.

Photoisomerizable Regulators

As noted above, a photoisomerizable regulator present in a conjugate of the present disclosure comprises: i) a photoisomerizable group; and ii) a ligand that binds to a target ligand-binding polypeptide.

Photoisomerizable Group

Photoisomerizable groups are known in the art, and any known photoisomerizable group can be included in the photoisomerizable regulator present in a conjugate of the present disclosure.

Suitable photoisomerizable groups include, but are not limited to, azobenzene, cyclic azobenzenes and azoheteroarenes and derivatives thereof; spiropyran and derivatives thereof; triphenyl methane and derivatives thereof; 4,5-epoxy-2-cyclopentene and derivatives thereof; fulgide and derivatives thereof; thioindigo and derivatives thereof; diarylethene and derivatives thereof; diallylethene and derivatives thereof; overcrowded alkenes and derivatives thereof; and anthracene and derivatives thereof. In some embodiments, a suitable photoisomerizable group is a photoisomerizable group as shown in the examples herein.

Suitable spiropyran derivatives include, but are not limited to, 1,3,3-trimethylindolinobenzopyrylospiran; 1,3,3-trimethylindolino-6'-nitrobenzopyrylospiran; 1,3,3-trimethylindolino-6'-bromobenzopyrylospiran; 1-n-decyl-3,3-dimethylindolino-6'-nitrobenzopyrylospiran; 1-n-octadecy-1-3,3-dimethylindolino-6'-nitrobenzopyrylospiran; 3',3'-dimethyl-6-nitro-1'-[2-(phenylcarbamoyl)ethyl]spiro; [2H-1-benzopyran-2,2'-indoline]; 1,3,3-trimetnylindolino-8'-methoxybenzopyrylospiran; and 1,3,3-trimethylindolino-β-naphthopyrylospiran. Also suitable for use is a merocyanine form corresponding to spiropyran or a spiropyran derivative.

Suitable triphenylmethane derivatives include, but are not limited to, malachite green derivatives. specifically, there can be mentioned, for example, bis[dimethylamino)phenyl] phenylmethanol, bis[4-(diethylamino)phenyl]phenylmethanol, bis[4-(dibuthylamino)phenyl]phenylmethanol and bis [4-(diethylamino)phenyl]phenylmethane.

Suitable 4,5-epoxy-2-cyclopentene derivatives include, for example, 2,3-diphenyl-1-indenone oxide and 2',3'-dimethyl-2,3-diphenyl-1-indenone oxide.

Suitable azobenzene compounds include, e.g., compounds having azobenzene residues crosslinked to a side chain, e.g., compounds in which 4-carboxyazobenzene is ester bonded to the hydroxyl group of polyvinyl alcohol or 4-carboxyazobenzene is amide bonded to the amino group of polyallylamine. Also suitable are azobenzene compounds having azobenzene residues in the main chain, for example, those formed by ester bonding bis(4-hydroxyphenyl)dimethylmethane (also referred to as bisphenol A) and 4,4'-dicarboxyazobenzene or by ester bonding ethylene glycol and 4,4'-dicarboxyazobenzene.

Suitable cyclic azobenzene and azoheteroarene compounds which can be adapted for use in the subject conjugates and photoisomerizable regulators include, but are not limited to, 11,12-dihydrodibenzo[c,g][1,2]diazocine-5-oxide,

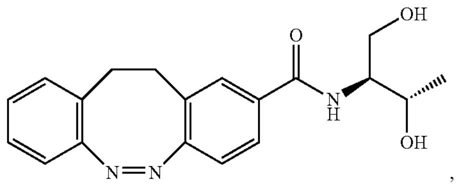 [SMILES: C[C@H](O)[C@H](CO)NC(=O)c1ccc2c(c1)CCc1ccccc1/N=N\2]
, heterodiazocines, such as those photoswitches described by Hammerich et al. J. Am. Chem. Soc., 2016, 138 (40), pp 13111-13114), and azoheteroarene photoswitches such as 3-pyrazoles (3pzH or 3pzMe), 5-pyrazoles (5pzH or 5pzMe), 3-pyrrroles (3pyH or 3pyMe), triazole and tetrazoles (tet or 3tri) as describes by Calbo et al. J. Am. Chem. Soc., 2017, 139 (3), pp 1261-1274, the disclosure of which is herein incorporated by reference.

Suitable fulgide derivatives include, but are not limited to, isopropylidene fulgide and adamantylidene fulgide.

Suitable diallylethene derivatives include, for example, 1,2-dicyano-1,2-bis(2,3,5-trimethyl-4-thienyl)ethane; 2,3-bis(2,3,5-trimethyl-4-thiethyl) maleic anhydride; 1,2-dicyano-1,2-bis(2,3,5-trimethyl-4-selenyl)ethane; 2,3-bis(2,3,5-trimethyl-4-selenyl) maleic anhydride; and 1,2-dicyano-1,2-bis(2-methyl-3-N-methylindole)ethane.

Suitable diarylethene derivatives include but are not limited to, substituted perfluorocylopentene-bis-3-thienyls and bis-3-thienylmaleimides.

Suitable overcrowded alkenes include, but are not limited to, cis-2-nitro-7-(dimethylamino)-9-(2',3'-dihydro-1'H-naphtho[2,1-b]thiopyran-1'-ylidene)-9H-thioxanthene and trans-dimethyl-[1-(2-nitro-thioxanthen-9-ylidene)-2,3-dihydro-1H-benzo[f]thiochromen-8-yl]amine. Overcrowded alkenes are described in the literature. See, e.g., terWiel et al. (2005) *Org. Biomol. Chem.* 3:28-30; and Geertsema et al. (1999) *Agnew CHem. Int. Ed. Engl.* 38:2738.

Other suitable photoisomerizable moieties include, e.g., reactive groups commonly used in affinity labeling, including diazoketones, aryl azides, diazerenes, and benzophenones.

Ligands

As used herein, the term "ligand" refers to a molecule (e.g., a small molecule, a peptide, or a protein) that binds to a polypeptide and effects a change in an activity of the polypeptide, and/or effects a change in conformation of the polypeptide, and/or affects binding of another polypeptide to the polypeptide, or affects the impact of another ligand on the polypeptide. Ligands include agonists, partial agonists, inverse agonists, antagonists, allosteric modulators, and blockers.

In some cases, the ligand is a naturally-occurring ligand. In other cases, the ligand is a synthetic ligand. In some cases, the ligand is an endogenous ligand. In some cases, the ligand is an agonist. In some cases, the ligand is an inverse agonist. In other cases, the ligand is a partial agonist. In other cases, the ligand is an antagonist. In other cases, the ligand is an allosteric modulator. In other cases, the ligand is a blocker. The term "antagonist" generally refers to an agent that binds to a ligand-binding polypeptide and inhibits the binding of the ligand-binding polypeptide. An "antagonist" may be an agent that binds to or near the orthosteric site (same site where an agonist binds) or an allosteric site but does not activate the ligand-binding polypeptide; instead, the antagonist generally excludes binding by an agonist or hinders activation by the agonist and thus prevents or hinders activation. An "allosteric modulator" may be an agent that binds to an allosteric site away from an orthosteric ligand binding site where binding of an allosteric ligand either decreases the sensitivity to or efficacy of an orthosteric ligand (negative allosteric modulator) or increases the sensitivity to or efficacy of an orthosteric ligand (positive allosteric modulator). The term "blocker" refers to an agent that acts directly on the active site, pore, or allosteric site. Ligands suitable for use herein bind reversibly to a ligand-binding site of a ligand-binding polypeptide.

The ligand is selected based in part on the target ligand-binding polypeptide, and the desired effect on the target ligand-binding polypeptide. For example, a ligand for a hormone-binding transcription factor will in some cases be a hormone, or a synthetic analog of the hormone, or a ligand that interferes with or modulates positively or negatively hormone binding or action. A ligand for a tetracycline transactivator will in some cases be tetracycline or a synthetic analog thereof. A ligand for an enzyme will in some cases be a synthetic agonist or antagonist of the enzyme. In some cases, a ligand will block the ligand-binding site. A ligand for an enzyme or ion channel will in some case be a blocker of the enzyme active site or ion channel pore. A ligand for a ligand-gated ion channel or a G protein coupled receptor or other membrane associated or soluble receptors will in some cases be a naturally-occurring ligand, or a synthetic version of the ligand, e.g., a synthetic analog of the ligand, or a ligand that interferes with or modulates positively or negatively the binding or action of that ligand.

In some cases, a ligand is a small molecule ligand. Small molecule ligands can have a molecular weight in a range of from about 50 daltons to about 3000 daltons, e.g., from about 50 daltons to about 75 daltons, from about 75 daltons to about 100 daltons, from about 100 daltons to about 250 daltons, from about 250 daltons to about 500 daltons, from about 500 daltons to about 750 daltons, from about 750 daltons to about 1000 daltons, from about 1000 daltons to about 1250 daltons, from about 1250 daltons to about 1500 daltons, from about 1500 daltons to about 2000 daltons, from about 2000 daltons to about 2500 daltons, or from about 2500 daltons to about 3000 daltons.

In other cases, a ligand is a peptide ligand. Peptide ligands can have a molecular weight in a range of from about 1 kDa to about 20 kDa, e.g., from about 1 kDa to about 2 kDa, from about 2 kDa to about 5 kDa, from about 5 kDa to about 7 kDa, from about 7 kDa to about 10 kDa, from about 10 kDa to about 12 kDa, from about 12 kDa to about 15 kDa, or from about 15 kDa to about 20 kDa. Peptide ligands can have a length of from 2 amino acids to 20 amino acids, e.g., a peptide ligand can have a length of 2, 3, 4, 5, 6, 7, 8, 9, 10, 11, 12, 13, 14, 15, 16, 17, 18, 19, or 20 amino acids. Peptide ligands can have a length of from 2 amino acids to 5 amino acids, from 5 amino acids to 10 amino acids, from 10 amino acids to 15 amino acids, or from 15 amino acids to 20 amino acids. Peptide ligands can be longer than 20 amino acids, e.g., up to 200 amino acids.

Suitable ligands include, but are not limited to, ligands that block or activate the function of a ligand-binding protein, where ligand-binding proteins include ion and macromolecule permeant channels; receptors (including, but not limited to, ionotropic receptors that bind transmitters; ionotropic receptors that bind hormones; metabotropic receptors and other G protein coupled receptors; receptor tyrosine kinases; growth factor receptors; and other membrane receptors that signal by binding to soluble or membrane-bound or extracellular small molecules or proteins); transporters (including but not limited to ion transporters, organic molecule transporters, peptide transporters, and protein transporters); enzymes (including but not limited to kinases; phosphatases; ubiquitin ligases; acetylases; oxo-reductases; lipases; enzymes that add lipid moieties to proteins or remove them; proteases; and enzymes that modify nucleic acids, including but not limited to ligases, helicases, topoisomerases, and telomerases); motor proteins (including kinesins, dyenins and other microtobule-based motors, myosins and other actin-based motors, DNA and RNA polymerases and other motors that track along polynucleotides); scaffolding proteins; adaptor proteins; cytoskeletal proteins; and other proteins that localize or organize protein domains and superstructures within cells.

Suitable ligands include, but are not limited to, ligands that function as general anesthetics; ligands that function as local anesthetics; ligands that function as analgesics; synthetic and semi-synthetic opioid analgesics (e.g., phenanthrenes, phenylheptylamines, phenylpiperidines, morphinans, and benzomorphans) where exemplary opioid analgesics include morphine, oxycodone, fentanyl, pentazocine, hydromorphone, meperidine, methadone, levorphanol, oxymorphone, levallorphan, codeine, dihydrocodeine, hydrocodone, propoxyphene, nalmefene, nalorphine, naloxone, naltrexone, buprenorphine, butorphanol, nalbuphine, and pentazocine; ionotropic glutamate receptor agonists and antagonists, e.g., N-methyl-D-aspartate (NMDA) receptor agonists, antagonists, and allosteric modulators, kainate (KA) receptor agonists and antagonists, and allosteric modulators, α-amino-3-hydroxy-5-methylisoxazole-4-propionic acid (AMPA) receptor agonists and antagonists and allosteric modulators, and metabotropic glutamate receptor agonists and antagonists and allosteric modulators; non-opioid analgesics, e.g., acetylsalicylic acid, choline magnesium trisalicylate, acetaminophen, ibuprofen, fenoprofen, diflusinal, and naproxen; muscarinic receptor agonists; muscarinic receptor antagonists; acetylcholine receptor agonists; acetylcholine receptor antagonists; serotonin receptor agonists; serotonin receptor antagonists; enzyme inhibitors; a benzodiazepine, e.g. chlordiazepoxide, clorazepate, diazepam, flurazepam, lorazepam, oxazepam, temazepam or triazolam; a barbiturate sedative, e.g. amobarbital, aprobarbital, butabarbital, butabital, mephobarbital, metharbital, methohexital, pentobarbital, phenobartital, secobarbital, talbutal, theamylal, or thiopental; an $H_1$ antagonist having a sedative action, e.g. diphenhydramine, pyrilamine, promethazine, chlorpheniramine, or chlorcyclizine; an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, topiramate, neramexane, or perzinfotel; an alpha-adrenergic, e.g. doxazosin, tamsulosin, clonidine, guanfacine, dexmetatomidine, modafinil, phentolamine, terazasin, prazasin or 4-amino-6,7-dimethoxy-2-(5-methane-sulfonamido-1,2,3,4-tetrahydroisoquinol-2-yl)-5-(2-pyridyl) quinazoline; a tricyclic antidepressant, e.g. desipramine, imipramine, amitriptyline, or nortriptyline; an anticonvulsant, e.g. carbamazepine, lamotrigine, topiratmate, or valproate; a tachykinin (NK) antagonist, particularly an NK-3, NK-2 or NK-1 antagonist, e.g. (α-R,9R)-7-[3,5-bis(trifluoromethyl) benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl) phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy) phenyl]-methylamino]-2-phenylpiperidine (2S,3S); a muscarinic antagonist, e.g oxybutynin, tolterodine, propiverine, tropsium chloride, darifenacin, solifenacin, temiverine, or ipratropium; a cyclooxygenase-2 (COX-2) selective inhibitor, e.g. celecoxib, rofecoxib, parecoxib, valdecoxib, deracoxib, etoricoxib, or lumiracoxib; a vanilloid receptor agonist (e.g. resinferatoxin) or antagonist (e.g. capsazepine); a beta-adrenergic such as propranolol; a 5-HT receptor agonist or antagonist, e.g., a $5\text{-HT}_1B/_1D$ agonist such as eletriptan, sumatriptan, naratriptan, zolmitriptan or rizatriptan; a $5\text{-HT}_2A$ receptor antagonist such as R(+)-α-(2,3-dimethoxy-phenyl)-1-[2-(4-fluorophenylethyl)]-4-piperidinemethanol (MDL-100907); and the like.

Suitable ligands for $Na^+$ channels include, but are not limited to, lidocaine, novocaine, xylocaine, lignocaine, novocaine, carbocaine, etidocaine, procaine, prontocaine, prilocaine, bupivacaine, cinchocaine, mepivacaine, quinidine, flecainide, procaine, N-[[2'-(aminosulfonyl)biphenyl-4-yl]methyl]-N'-(2,2'-bithien-5-ylmethyl)succinamide (BPBTS), QX-314, saxitoxin, tetrodotoxin, and a type III conotoxin. Suitable ligands for $Na^+$ channels also include, but are not limited to, tetrodotoxin, saxitoxin, guanidinium, polyamines (e.g. spermine, cadaverine, putrescine, μ-conotoxin, and δ-conotoxin.

Suitable ligands for $K^+$ channels include, but are not limited to, quaternary ammonium (e.g., tetraethyl ammonium, tetrabutylammonium, tetrapentylammonium), 4-aminopyridine, sulfonylurea, Glibenclamide; Tolbutamide; Phentolamine, qiunine, qunidine, peptide toxins (e.g., charybdotoxin, agitoxin-2, apamin, dendrotoxin, VSTX1, hanatoxin-1, hanatoxin-2, and Tityus toxin K-α.

Suitable ligands for CNG and HCN channels include, but are not limited to, 1-cis diltiazem and ZD7288. Suitable ligands for glycine receptors include, but are not limited to, strychnine and picrotoxin.

Suitable ligands for nicotinic acetylcholine receptors include, but are not limited to, (+)tubocurarine, Methyllycaconitine, gallamine, Nicotine; Anatoxin A, epibatidine, ABT-94, Lophotoxin, Cytisine, Hexamethonium, Mecamylamine, and Dihydro-β-erythroidine. Suitable ligands for muscarinic acetylcholine receptors include, but are not limited to, a muscarinic acetylcholine receptor antagonist as described in U.S. Pat. No. 7,439,255; AF267B (see, e.g., U.S. Pat. No. 7,439,251); phenylpropargyloxy-1,2,5-thiadiazole-quinuclidine; carbachol; pirenzapine; migrastatin; a compound as described in U.S. Pat. No. 7,232,841; etc.

Suitable ligands for GABA receptors include, but are not limited to, Muscimol, THIP, Procabide, bicuculine, picrotoxin, gabazine, gabapentin, diazepam, clonazepam, flumazenil, α-carboline carboxylate ethyl ester, baclofen, faclofen, and a barbiturate.

Many suitable ligands will be known to those skilled in the art; and the choice of ligand will depend, in part, on the target (e.g., receptor, ion channel, enzyme, etc.) to which the ligand binds.

Conjugate and Photoisomerizable Regulator Formulas

In some cases, a conjugate including a photoisomerizable regulator of the present disclosure is a compound having the formula: (A)-$X_1$—(B)-$X_2$-(C), where:

A is an affinity agent;

B is a photoisomerizable group;

C is a ligand;

$X_1$, when present, is a linker; and $X_2$, when present, is a linker.

Suitable ligands include those described above. In some cases, the ligand is a sodium channel ligand, a synthetic ligand, a ligand that binds to a ligand binding site of an ionotropic receptor, a ligand that binds to a ligand binding site of a metabotropic receptor, a ligand that functions as an anesthetic, a potassium channel ligand, a gamma aminobutyric acid receptor ligand. In some of these embodiments, the ligand is a sodium channel ligand, a potassium channel ligand, or a gamma aminobutyric acid receptor ligand. In some cases, the ligand is an agonist, an antagonist, an allosteric modulator, or a blocker.

Any convenient photoswitch or photoisomerizable group can be adapted for use in the conjugates and photoisomerizable regulators of the present disclosure. Photoswitch or photoisomerizable groups of interest, include those described in U.S. Pat. Nos. 8,114,843, 8,178,496 and WO2010/051343, the disclosures of which are herein incorporated by reference in their entirety.

In some cases, a conjugate of the present disclosure is a compound having the formula: (A)-$X_1$-(B)-$X_2$-(C), where:

A is an affinity agent;

B is a photoisomerizable group selected from an azobenzene, cyclic azobenzene, an azoheteroarene, a fulgide, a spiropyran, a triphenyl methane, a thioindigo, a diarylethene, or an overcrowded alkene;

C is a ligand;

$X_1$, when present, is a linker; and $X_2$, when present, is a linker.

Suitable linkers include, but are not limited to, a polycarbon chain; poly(ethylene glycol); a peptide; and the like. In some cases, the linker is a $C_1$-$C_{25}$ alkyl. In some cases, the linker is a substituted $C_1$-$C_{25}$ alkyl. In some cases, the linker is poly(ethylene glycol) (PEG), where the PEG comprises from 2 to 50 ethylene glycol monomers; e.g., the PEG comprises from 2 to 5, from 5 to 10, from 10 to 15, from 15 to 20, from 20 to 25, from 25 to 30, from 30 to 35, from 35 to 40, from 40 to 45, or from 45 to 50, ethylene glycol units. In some cases, the linker is a peptide of from 2 amino acids to 50 amino acids; e.g., from 2 amino acids to 5 amino acids, from 5 amino acids to 10 amino acids, from 10 amino acids to 15 amino acids, from 15 amino acids to 20 amino acids, from 20 amino acids to 25 amino acids, from 25 amino acids to 30 amino acids, or from 30 amino acids to 50 amino acids. In some cases, the linker is a peptide of 2, 3, 4, 5, 6, 7, 8, 9, or 10 amino acids in length.

Suitable ligands include those described above. In some cases, the ligand is a sodium channel ligand, a synthetic ligand, a ligand that binds to a ligand binding site of an ionotropic receptor, a ligand that binds to a ligand binding site of a metabotropic receptor, a ligand that functions as an anesthetic, a potassium channel ligand, a gamma aminobutyric acid receptor ligand. In some instances, the ligand is a sodium channel ligand, a potassium channel ligand, or a gamma aminobutyric acid receptor ligand. In some cases, the ligand is an agonist, an antagonist, an allosteric modulator, or a blocker.

In some cases, a photoisomerizable regulator suitable for inclusion in a conjugate of the present disclosure comprises: i) a chemoselective functional group (CFG) that covalently links to an affinity agent having a compatible reactive functional group (e.g., as described herein, e.g., an antibody); ii) a linker; iii) a photoisomerizable moiety; and iv) a ligand. For example, a compound of formula CFG-$X_1$—(B)—$X_2$—(C) that is capable of conjugation to an affinity agent (A). As used herein, the terms "chemoselective functional group" and "chemoselective tag" are used interchangeably and refer to a functional group that can selectively react with another compatible functional group to form a covalent bond, in some cases, after optional activation of one of the functional groups. Chemoselective functional groups of interest include, but are not limited to, thiols and maleimide or iodoacetamide, amines and carboxylic acids or active esters thereof, as well as groups that can react with one another via Click chemistry, e.g., azide and alkyne groups (e.g., cyclooctyne groups), tetrazine, transcyclooctene, dienes and dienophiles, and azide, sulfur(VI) fluoride exchange chemistry (SuFEX), sulfonyl fluoride, as well as hydroxyl, hydrazido, hydrazino, aldehyde, ketone, azido, alkyne, phosphine, epoxide, and the like.

In some cases, a photoisomerizable regulator suitable for inclusion in a conjugate of the present disclosure comprises: i) a moiety that covalently links to a SNAP tag, a HALO tag, a CLIP tag, or other affinity tag; ii) a linker; iii) a photoisomerizable moiety; and iv) a ligand. For example, in some cases, a photoisomerizable regulator suitable for inclusion in a conjugate of the present disclosure comprises: i) benzylguanine (for covalent binding to a SNAP tag, such as a SNAP tag present in an antibody-SNAP tag fusion polypeptide); ii) a linker; iii) a photoisomerizable moiety; and iv) a ligand. As another example, in some cases, a photoisomerizable regulator suitable for inclusion in a conjugate of the present disclosure comprises: i) chloroalkane (for covalent binding to a HALO tag, such as a HALO tag present in an antibody-HALO tag fusion polypeptide; ii) a linker; iii) a photoisomerizable moiety; and iv) a ligand. As another example, in some cases, a photoisomerizable regulator suitable for inclusion in a conjugate of the present disclosure comprises: i) benzylcytosine (for covalent binding to a CLIP tag, such as a CLIP tag present in an antibody-CLIP tag fusion polypeptide; ii) a linker; iii) a photoisomerizable moiety; and iv) a ligand.

In certain instances, a photoisomerizable regulator present in a conjugate of the present disclosure functions as a blocker (e.g., a potassium channel blocker, and/or a sodium channel blocker and/or a calcium channel blocker) in the cis-isomeric form. In other cases, a photoisomerizable regulator present in a conjugate of the present disclosure functions as a blocker (e.g., a potassium channel blocker, and/or a sodium channel blocker and/or a calcium channel blocker) in the trans-isomeric form.

In some instances, the photoisomerizable group of the conjugate (e.g., as defined herein) is an azobenzene or azoheteroarene photoswitch of one of the following formula:

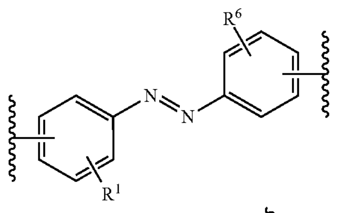

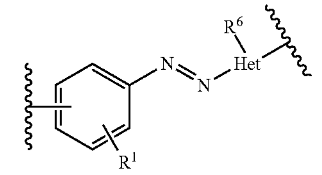

wherein:

Het is a heteroaryl or substituted heteroaryl;

$R^1$ and $R^6$ are one or more optional substituents selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted C4-10 cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$, wherein $R^{10}$-$R^{13}$ are as defined below, or wherein $R^1$ and $R^6$ are cyclically linked to provide a cyclic azobenzene or cyclic azoheteroarene.

In some cases, a photoisomerizable regulator present in a conjugate of the present disclosure is derived from a compound of Formula I:

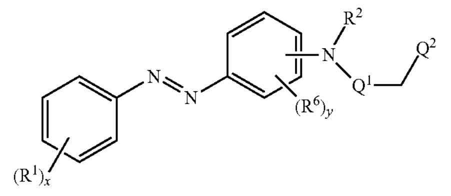

wherein $Q^1$ is —$CH_2$— or —C(=O)—;

$Q^2$ is

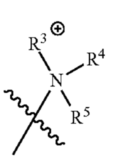

or

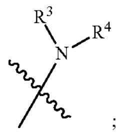

;

each of $R^1$ is independently selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted C4-10 cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

x is an integer from 1 to 5;

y is an integer from 1 to 4;

$R^2$ is selected from hydrogen, $C_{1-10}$ alkyl, substituted $C_{1-10}$ alkyl, C2-10 alkenyl, substituted $C_{2-10}$ alkenyl, $C_{2-10}$ alkynyl, substituted $C_{2-10}$ alkynyl, C6-20 aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

$R^3$, $R^4$, and $R^5$ are independently selected from hydrogen, $C_2$-$C_8$ alkyl, substituted $C_{2-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

each of $R^6$ is independently selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

$R^{10}$ and $R^{11}$ are independently selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

$R^{12}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

$R^{13}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_6$-$C_{10}$ aryl, substituted $C_{6-20}$ aryl, $C_{4-10}$ cycloalkyl, substituted $C_{4-10}$ cycloalkyl, $C_{4-10}$ cycloalkenyl, substituted $C_{4-10}$ cycloalkenyl, —$CH_2$—$N(CH_2CH_3)_3^+$, and —$CH_2$—$SO_3^-$;

or a pharmaceutically acceptable salt thereof.

In some cases, a photoisomerizable regulator present in a conjugate of the present disclosure is a compound of Formula II:

(Formula II)

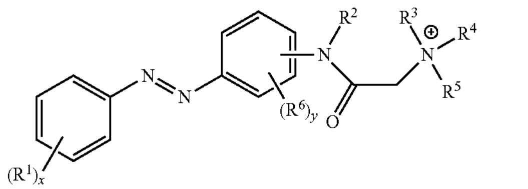

wherein each of $R^1$ is independently selected from hydrogen, $C_{1-10}$ alkyl, substituted $C_{1-10}$ alkyl, —$NR^{10}R^{11}$, —$NR^2C(O)R^3$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

x is an integer from 1 to 5;

y is an integer from 1 to 4;

$R^2$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

$R^3$, $R^4$, and $R^5$ are independently selected from hydrogen, C2-8 alkyl, substituted $C_{2-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

each of $R^6$ is independently selected from hydrogen, $C_{1-10}$ alkyl, substituted $C_{1-10}$ alkyl, —$NR^{10}$R11, —$NR^{12}C(O)R^{13}$, $C_{2-10}$ alkenyl, substituted $C_{2-10}$alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-0}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

$R^{10}$ and $R^{11}$ are independently selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

$R^{12}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{240}$ alkynyl, C6-20 aryl, substituted C6-20 aryl, $C_{4-10}$ cycloalkyl, substituted $C_{4-10}$ cycloalkyl, $C_{4-10}$ cycloalkenyl, and substituted $C_{4-10}$ cycloalkenyl;

$R^{13}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-10}$ aryl, substituted $C_{6-20}$ aryl, $C_{4-10}$ cycloalkyl, substituted $C_{4-10}$ cycloalkyl, $C_{4-10}$ cycloalkenyl, substituted $C_{4-10}$ cycloalkenyl, —$CH_2$—$N(CH_2CH_3)^{3+}$, and —$CH_2$—$SO_3^-$;

or a pharmaceutically acceptable salt thereof.

In some instances of Formula (I), one of $R^1$ is a linker comprising a chemoselective functional group capable of covalently linking to an affinity agent (e.g., as described herein). In some instances of Formula (I), one of $R^1$ is a linker to a linked affinity agent (e.g., as described herein).

In certain embodiments of Formula I, $Q^1$ is —$CH_2$—. In certain embodiments of Formula I, $Q^1$ is —C(=O)—.

In certain embodiments of Formula I, $Q^2$ is

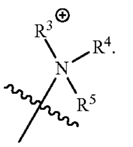

In certain embodiments of Formula I, $Q^2$ is

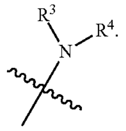

In certain embodiments of any one of the above Formulae I and II, $R^3$, $R^4$, and $R^5$ are $C_{2-10}$ alkyl. In certain embodiments of any one of the above Formulae I and II, $R^3$, $R^4$, and $R^5$ are $C_{2-5}$ alkyl. In certain embodiments of any one of the above Formulae I and II, $R^3$, $R^4$, and $R^5$ are $C_2$ alkyl. In certain embodiments of any one of the above Formulae I and II, $R^3$, $R^4$, and $R^5$ are $C_3$ alkyl. In certain embodiments of any one of the above Formulae I and II, $R^3$, $R^4$, and $R^5$ are $C_4$ alkyl. In certain embodiments of Formulae I and II, $R^3$, $R^4$, and $R^5$ are hydrogen.

In certain embodiments of any one of the above Formulae I and II, $R^3$, $R^4$, and $R^5$ are independently selected from $C_{2-8}$ alkyl or substituted $C_{2-8}$ alkyl. In certain embodiments of any one of the above Formulae I and II, $R^3$, $R^4$, and $R^5$ are independently selected from $C_{2-10}$ alkenyl, substituted $C_{2-10}$ alkenyl, $C_{2-10}$ alkynyl, substituted $C_{2-10}$ alkynyl. In certain embodiments of any one of the above Formulae I and II, $R^3$, $R^4$, and $R^5$ are independently selected from $C_{6-20}$ aryl or substituted $C_{6-20}$ aryl. In certain embodiments of any one of the above Formulae I and II, $R^3$, $R^4$, and $R^5$ are independently selected from $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae I and II, $R^2$ is hydrogen. In certain embodiments of any one of the above Formulae I and II, $R^2$ is $C_{1-10}$ alkyl. In certain embodiments of any one of the above Formulae I and II, $R^2$ is $C_{1-5}$ alkyl. In certain embodiments of any one of the above Formulae I and II, $R^2$ is hydrogen or $C_{1-5}$ alkyl.

In certain embodiments of any one of the above Formulae I and II, $R^2$ is $C_{1-10}$ alkyl or substituted $C_{1-10}$ alkyl. In certain embodiments of any one of the above Formulae I and II, $R^2$ is $C_{2-10}$ alkenyl, substituted $C_{2-10}$ alkenyl, $C_{2-10}$ alkynyl, substituted $C_{2-10}$ alkynyl. In certain embodiments of any one of the above Formulae I and II, $R^2$ is $C_{6-20}$ aryl or substituted $C_{6-20}$ aryl. In certain embodiments of any one of the above Formulae I and II, $R^2$ is $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae I and II, at least one of $R^6$ is $C_{1-10}$ alkyl, substituted $C_{1-10}$ alkyl, or halo. In certain embodiments of any one of the above Formulae I and II, at least one of $R^6$ is $C_{1-4}$ alkyl. In certain embodiments of any one of the above Formulae I and II, at least one of $R^6$ is halo.

In certain embodiments of any one of the above Formulae I and II, at least one of $R^6$ is $—NR^{10}R^{11}$ or $—NR^{12}C(O)R^{13}$. In certain embodiments of any one of the above Formulae I and II, at least one of $R^6$ is $C_{2-10}$ alkenyl, substituted $C_{2-10}$ alkenyl, $C_{2-10}$ alkynyl, or substituted $C_{2-10}$ alkynyl.

In certain embodiments of any one of the above Formulae I and II, at least one of $R^6$ is $C_{6-20}$ aryl, substituted $C_{6-20}$ aryl, heteroaryl, or heterocyclic. In certain embodiments of any one of the above Formulae I and II, at least one of $R^6$ is heterocyclooxy, heterocyclothio, heteroarylamino, or heterocycloamino. In certain embodiments of any one of the above Formulae I and II, at least one of $R^6$ is $C_{4-10}$ cycloalkyl, substituted $C_{4-10}$ cycloalkyl, $C_{4-10}$ cycloalkenyl, or substituted $C_{4-10}$ cycloalkenyl. In certain embodiments of any one of the above Formulae I and II, at least one of $R^6$ is cyano, halo, $—OR^{10}$, $—C(O)OR^{10}$, $—SR^{10}$, $—S(O)R^{10}$, or $—S(O)_2R^{10}$.

In certain embodiments of any one of the above Formulae I and II, at least one of $R^1$ is hydrogen.

In certain embodiments of any one of the above Formulae I and II, at least one of $R^1$ is $C_{1-8}$ alkyl, e.g., $C_{1-6}$ alkyl, $C_{1-5}$ alkyl or $C_{1-4}$ alkyl. In some embodiments of any one of the above Formulae I and II, at least one of $R^1$ is $C_{1-4}$ alkyl.

In certain embodiments of any one of the above Formulae I and II, at least one of $R^1$ is $—NR^{12}C(O)R^{13}$.

In certain embodiments of any one of the above Formulae I and II, at least one of $R^1$ is $—NR^{10}R^{11}$.

In certain embodiments of any one of the above Formulae I and II, at least one of $R^1$ is $C_{1-10}$ alkyl or substituted $C_{1-10}$ alkyl.

In certain embodiments of any one of the above Formulae I and II, at least one of $R^1$ is $C_{2-10}$ alkenyl, substituted $C_{2-10}$ alkenyl, $C_{2-10}$ alkynyl, or substituted $C_{2-10}$ alkynyl. In certain embodiments of any one of the above Formulae I and II, at least one of $R^1$ is $C_{6-20}$ aryl or substituted $C_{6-20}$ aryl. In certain embodiments of any one of the above Formulae I and II, at least one of $R^1$ is heteroaryl, heterocyclic, heterocyclooxy, heterocyclothio, heteroarylamino, or heterocycloamino. In certain embodiments of any one of the above Formulae I and II, at least one of $R^1$ is $C_{4-10}$ cycloalkyl, substituted $C_{4-10}$ cycloalkyl, $C_{4-10}$ cycloalkenyl, or substituted $C_{4-10}$ cycloalkenyl. In certain embodiments of any one of the above Formulae I and II, at least one of $R^1$ is cyano, halo, $—OR^{10}$, $—C(O)OR^{10}$, $—SR^{10}$, $—S(O)R^{10}$, $—S(O)_2R^{10}$.

In certain embodiments of any one of the above Formulae I and II, $R^{12}$ is hydrogen. In certain embodiments of any one of the above Formulae I and II, $R^{12}$ is $C_{1-10}$ alkyl. In certain embodiments of any one of the above Formulae I and II, $R^{12}$ is $C_{1-5}$ alkyl. In certain embodiments of any one of the above Formulae I and II, $R^{12}$ is hydrogen or $C_{1-5}$ alkyl.

In certain embodiments of any one of the above Formulae I and II, $R^{12}$ is hydrogen. In certain embodiments of any one of the above Formulae I and II, $R^{12}$ is $C_{1-10}$ alkyl or substituted $C_{1-10}$ alkyl. In certain embodiments of any one of the above Formulae I and II, $R^{12}$ is $C_{2-10}$ alkenyl, substituted $C_{2-10}$ alkenyl, $C_{2-10}$ alkynyl, or substituted $C_{2-10}$ alkynyl. In certain embodiments of any one of the above Formulae I and II, $R^{12}$ is $C_{6-20}$ aryl or substituted $C_{6-20}$ aryl. In certain embodiments of any one of the above Formulae I and II, $R^{12}$ is $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae I and II, $R^{13}$ is hydrogen or $C_{1-10}$ alkyl. In certain embodiments of any one of the above Formulae I and II, $R^{13}$ is $C_{1-10}$ alkyl. In certain embodiments of any one of the above Formulae I and II, $R^{13}$ is $C_{1-5}$ alkyl. In certain embodiments of any one of the above Formulae I and II, $R^{13}$ is hydrogen or $C_{1-5}$ alkyl.

In certain embodiments of any one of the above Formulae I and II, $R^{13}$ is alkenyl or substituted alkenyl. In certain embodiments of any one of the above Formulae I and II, $R^{13}$ is $C_{1-10}$ alkenyl. In certain embodiments of any one of the above Formulae I and II, $R^{13}$ is $C_{1-5}$ alkenyl. In certain embodiments of any one of the above Formulae I and II, $R^{13}$ is hydrogen or $C_{1-5}$ alkenyl.

In certain embodiments of any one of the above Formulae I and II, $R^{13}$ is $C_6$ aryl or substituted $C_6$ aryl.

In certain embodiments of any one of the above Formulae I and II, $R^{13}$ is —$CH_2$—$N(CH_2CH_3)_3^+$ or —$CH_2$—$SO_3^-$. In certain embodiments of any one of the above Formulae I and II, $R^{13}$ is —$CH_2$—$N(CH_2CH_3)_3^+$. In certain embodiments of any one of the above Formulae I and II, $R^{13}$ is or —$CH_2$—$SO_3^-$.

In certain embodiments of any one of the above Formulae I and II, $R^{13}$ is hydrogen. In certain embodiments of any one of the above Formulae I and II, $R^{13}$ is $C_{1-10}$ alkyl or substituted $C_{1-10}$ alkyl. In certain embodiments of any one of the above Formulae I and II, $R^{13}$ is $C_{2-10}$ alkenyl or substituted $C_{2-10}$ alkenyl. In certain embodiments of any one of the above Formulae I and II, $R^{13}$ is $C_{2-10}$ alkynyl or substituted $C_{2-10}$ alkynyl. In certain embodiments of any one of the above Formulae I and II, $R^{13}$ is $C_{6-10}$ aryl or substituted $C_{6-20}$ aryl. In certain embodiments of any one of the above Formulae I and II, $R^{13}$ is $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae I and II, at least one of $R^{10}$ and $R^{11}$ is hydrogen. In certain embodiments of any one of the above Formulae I and II, at least one of $R^{10}$ and $R^{11}$ is $C_{1-10}$ alkyl or substituted $C_{1-10}$ alkyl. In certain embodiments of any one of the above Formulae I and II, at least one of $R^{10}$ and $R^{11}$ is $C_{2-10}$ alkenyl, substituted $C_{2-10}$ alkenyl, $C_{2-10}$ alkynyl, or substituted $C_{2-10}$ alkynyl. In certain embodiments of any one of the above Formulae I and II, at least one of $R^{10}$ and $R^{11}$ is $C_{6-20}$ aryl or substituted $C_{6-20}$ aryl. In certain embodiments of any one of the above Formulae I and II, at least one of $R^{10}$ and $R^{11}$ is $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae I and II, at least one of $R^{10}$ and $R^{11}$ is $C_{1-10}$ alkyl. In certain embodiments of any one of the above Formulae I and II, at least one of $R^{10}$ and $R^{11}$ is $C_{2-5}$ alkyl. In certain embodiments of any one of the above Formulae I and II, at least one of $R^{10}$ and $R^{11}$ is $C_2$ alkyl. In certain embodiments of any one of the above Formulae I and II, at least one of $R^{10}$ and $R^{11}$ is $C_3$ alkyl. In certain embodiments of any one of the above Formulae I and II, at least one of $R^{10}$ and $R^{11}$ is $C_4$ alkyl.

In certain embodiments of any one of the above Formulae I and II, at least one of $R^{10}$ and $R^{11}$ is alkyl substituted with aryl, aryloxy, heteroaryl, heteroaryloxy, heterocyclic, or heterocyclooxy. In certain embodiments of any one of the above Formulae I and II, at least one of $R^{10}$ and $R^{11}$ is alkyl substituted with aryl, heteroaryl, or heterocyclic. In certain embodiments of any one of the above Formulae I and II, at least one of $R^{10}$ and $R^{11}$ is alkyl substituted with aryl. In certain embodiments of any one of the above Formulae I and II, at least one of $R^{10}$ and $R^{11}$ is alkyl substituted with heteroaryl. In certain embodiments of any one of the above Formulae I and II, at least one of $R^{10}$ and $R^{11}$ is alkyl substituted with heterocyclic.

In some embodiments, a photoisomerizable regulator present in a conjugate of the present disclosure is a compound of Formula III:

(Formula III)

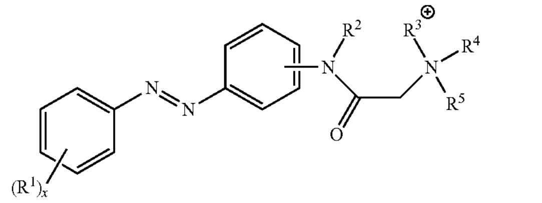

wherein each of $R^1$ is independently selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

x is an integer from 1 to 5;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-10}$ alkenyl, $C_{6-10}$ aryl, and substituted $C_{1-10}$ alkyl, or a pharmaceutically acceptable salt thereof.

In some cases, a photoisomerizable regulator present in a conjugate of the present disclosure is a compound of Formula IV:

(Formula IV)

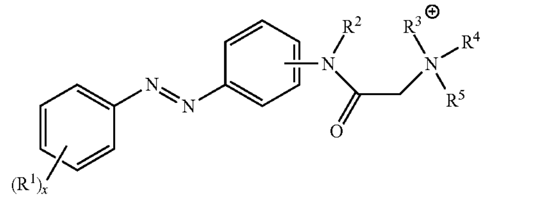

wherein each of $R^1$ are independently selected from hydrogen, $C_{1-10}$ alkyl, —$NR^{10}R^{11}$, —$NR^{12}C(O)R^{13}$, $C_{2-10}$ alkenyl, $C_{2-10}$ alkynyl, cyano, halo, —$OR^{10}$, —$C(O)OR^{10}$, —$SR^{10}$, —$S(O)R^{10}$, —$S(O)_2R^{10}$;

x is an integer from 1 to 5;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some cases, a photoisomerizable regulator present in a conjugate of the present disclosure is a compound of Formula V:

(Formula V)

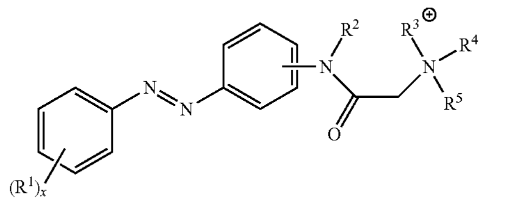

wherein each of $R^1$ are independently selected from hydrogen, $C_{1-10}$ alkyl, $—NR^{10}R^{11}$, and $—NR^{12}C(O)R^{13}$;

x is an integer from 1 to 5;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some cases, a photoisomerizable regulator present in a conjugate of the present disclosure is a compound of Formula VI:

(Formula VI)

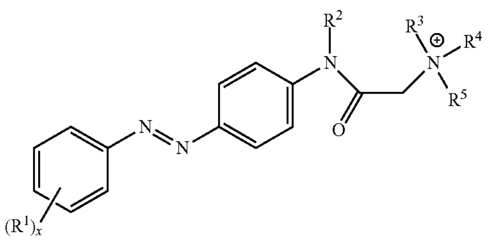

wherein each of $R^1$ are independently selected from hydrogen, $C_{1-10}$ alkyl, $—NR^{10}R^{11}$, and $—NR^{12}C(O)R^{13}$;

x is an integer from 1 to 5;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some cases, a photoisomerizable regulator present in a conjugate of the present disclosure is a compound of Formula VII:

(Formula VII)

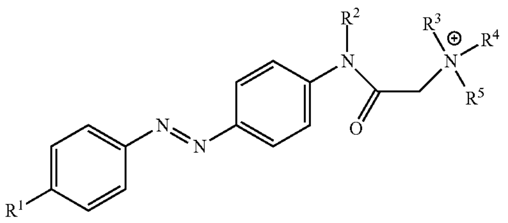

wherein $R^1$ is selected from hydrogen, $C_{1-10}$ alkyl, $—NR^{10}R^{11}$, and $—NR^{12}C(O)R^{13}$;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some cases, a photoisomerizable regulator present in a conjugate of the present disclosure is a compound of Formula VIII:

(Formula VIII)

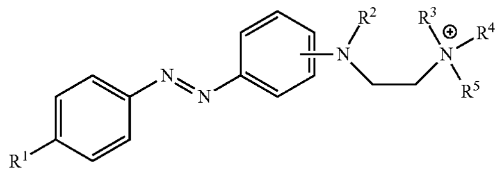

wherein $R^1$ is selected from hydrogen, $C_{1-10}$ alkyl, substituted $C_{1-10}$ alkyl, $—NR^{10}R^{11}$, $—NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $—OR^{10}$, $—C(O)OR^{10}$, $—SR^{10}$, $—S(O)R^{10}$, $—S(O)_2R^{10}$;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{11}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof. In some cases, a compound of Formula VIII has no carbonyl group.

In some cases, a photoisomerizable regulator present in a conjugate of the present disclosure is a compound of Formula IX:

(Formula IX)

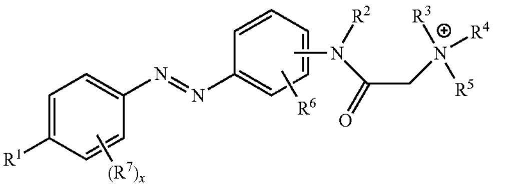

wherein $R^1$ is selected from hydrogen, $C_{1-10}$ alkyl, substituted $C_{1-10}$ alkyl, $—NR^{10}R^{11}$, $—NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $—OR^{10}$, $—C(O)OR^{10}$, $—SR^{10}$, $—S(O)R^{10}$, $—S(O)_2R^{10}$;

x is an integer from 1 to 4;

$R^2$ is hydrogen or $C_{1-10}$ alkyl;

$R^3$, $R^4$, and $R^5$ are independently selected from hydrogen and $C_{2-8}$ alkyl;

each of $R^6$ and $R^7$ are independently selected from hydrogen, $C_{1-10}$ alkyl, substituted $C_{1-10}$ alkyl, $—NR^{10}R^{11}$, $—NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $—OR^{10}$, $—C(O)OR^{10}$, $—SR^{10}$, $—S(O)R^{10}$, $—S(O)_2R^{10}$;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some cases, a photoisomerizable regulator present in a conjugate of the present disclosure is a compound of Formula X:

(Formula X)

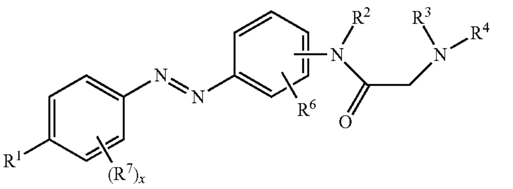

wherein $R^1$ is selected from hydrogen, $C_{1-10}$ alkyl, substituted $C_{1-10}$ alkyl, $—NR^{10}R^{11}$, $—NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $—OR^{10}$, $—C(O)OR^{10}$, $—SR^{10}$, $—S(O)R^{10}$, $—S(O)_2R^{10}$;

x is an integer from 1 to 4;

$R^2$ is hydrogen or $C_{1-10}$ alkyl;

$R^3$ and $R^4$ are independently selected from hydrogen and $C_{2-8}$ alkyl;

each of $R^6$ and $R^7$ are independently selected from hydrogen, $C_{1-10}$ alkyl, substituted $C_{1-10}$ alkyl, $—NR^{10}R^{11}$, $—NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$cycloalkenyl, substituted $C_{4-10}$cycloalkenyl, cyano, halo, $—OR^{10}$, $—C(O)OR^{10}$, $—SR^{10}$, $—S(O)R^{10}$, $—S(O)_2R^{10}$;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof. In some cases, the nitrogen is not permanently charged.

In some cases, a photoisomerizable regulator present in a conjugate of the present disclosure is a compound of Formula XI:

(Formula XI)

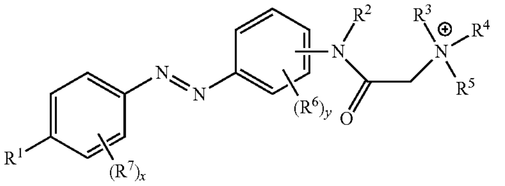

wherein $R^1$ is selected from hydrogen, $C_{1-10}$ alkyl, substituted $C_{1-10}$ alkyl, $—NR^{10}R^{11}$, $—NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $—OR^{10}$, $—C(O)OR^{10}$, $—SR^{10}$, $—S(O)R^{10}$, $—S(O)_2R^{10}$;

x is an integer from 1 to 4;

y is an integer from 1 to 4;

$R^2$ is hydrogen or $C_{1-10}$ alkyl;

$R^3$, $R^4$, and $R^5$ are independently selected from hydrogen and $C_{2-8}$ alkyl;

each of $R^6$ and $R^7$ are independently selected from hydrogen, $C_{1-10}$ alkyl, substituted $C_{1-10}$ alkyl, $NR^{10}R^{11}$, $—NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $—OR^{10}$, $—C(O)OR^{10}$, $—SR^{10}$, $—S(O)R^{10}$, $—S(O)_2R^{10}$;

$R^{10}$ and $R^{11}$ are independently selected from hydrogen and $C_{1-10}$ alkyl;

$R^{12}$ is hydrogen or $C_{1-10}$ alkyl;

$R^{11}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some cases, a photoisomerizable regulator present in a conjugate of the present disclosure is a compound of Formula XII:

(Formula XII)

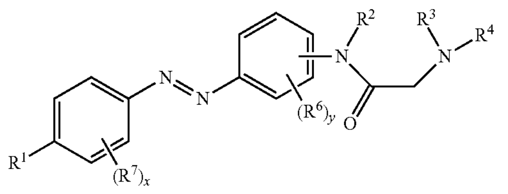

wherein $R^1$ is selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

x is an integer from 1 to 4;

y is an integer from 1 to 4;

$R^2$ is hydrogen or $C_{1-10}$ alkyl;

$R^3$ and $R^4$ are independently selected from hydrogen and $C_{2-8}$ alkyl;

each of $R^6$ and $R^7$ are independently selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In certain embodiments of any one of the above Formulas III-XII, $R^2$ is hydrogen. In certain embodiments of any one of the above Formulas III-XII, $R^2$ is $C_{1-10}$ alkyl. In certain embodiments of any one of the above Formulas III-XII, $R^2$ is $C_{1-5}$ alkyl. In certain embodiments of any one of the above Formulas III-XII, $R^2$ is hydrogen or $C_{1-5}$ alkyl.

In certain embodiments of any one of the above Formulas III-XII, $R^1$ is hydrogen.

In certain embodiments of any one of the above Formulas III-XII, $R^1$ is $C_{1-8}$ alkyl, e.g., $C_{1-6}$ alkyl, $C_{1-5}$ alkyl or $C_{1-4}$ alkyl. In some embodiments of any one of the above Formulas III-XII, $R^1$ is $C_{1-4}$ alkyl.

In certain embodiments of any one of the above Formulas III-XII, $R^1$ is —$NR^{12}C(O)R^{13}$.

In certain embodiments of any one of the above Formulas III-XII, $R^{12}$ is hydrogen. In certain embodiments of any one of the above Formulas III-XII, $R^{12}$ is $C_{1-10}$ alkyl. In certain embodiments of any one of the above Formulas III-XII, $R^{12}$ is $C_{1-5}$ alkyl. In certain embodiments of any one of the above Formulas III-XII, $R^{12}$ is hydrogen or $C_{1-5}$ alkyl.

In certain embodiments of any one of the above Formulas III-XII, $R^{13}$ is hydrogen or $C_{1-10}$ alkyl. In certain embodiments of any one of the above Formulas III-XII, $R^{13}$ is $C_{1-10}$ alkyl. In certain embodiments of any one of the above Formulas III-XII, $R^{13}$ is $C_{1-5}$ alkyl. In certain embodiments of any one of the above Formulas III-XII, $R^{13}$ is hydrogen or $C_{1-5}$ alkyl.

In certain embodiments of any one of the above Formulas III-XII, $R^{13}$ is alkenyl or substituted alkenyl. In certain embodiments of any one of the above Formulas III-XII, $R^{13}$ is $C_{1-10}$ alkenyl. In certain embodiments of any one of the above Formulas III-XII, $R^{13}$ is $C_{1-5}$ alkenyl. In certain embodiments of any one of the above Formulas III-XII, $R^{13}$ is hydrogen or $C_{1-5}$ alkenyl.

In certain embodiments of any one of the above Formulas III-XII, $R^{13}$ is $C_6$ aryl or substituted $C_6$ aryl.

In certain embodiments of any one of the above Formulas III-XII, $R^{13}$ is alkyl substituted with $SO_3H$, —$SO_3^-$, —$NR_aR_b$, —$N^+R_aR_bR_c$, wherein $R_a$, $R_b$, and $R_c$ may be the same or different and are chosen from hydrogen, optionally substituted alkyl, cycloalkyl, alkenyl, cycloalkenyl, alkynyl, aryl, heteroaryl and heterocyclic. In certain embodiments of any one of the above Formulas III-XII, $R^{13}$ is alkyl substituted with $SO_3H$ or —$SO_3^-$. In certain embodiments of any one of the above Formulas III-XII, $R^{13}$ is alkyl substituted with —$NR_aR_b$ or —$N^+R_aR_bR_c$, In certain embodiments of any one of the above Formulas III-XII, $R^{13}$ is alkyl substituted with —$NR_aR_b$ or —$N^+R_aR_bR_c$, and wherein $R_a$, $R_b$, and $R_c$ may be the same or different and are chosen from hydrogen and optionally substituted alkyl. In certain embodiments of any one of the above Formulas III-XII, $R^{13}$ is alkyl substituted with —$NR_aR_b$ or —$NR_aR_bR_c$, and wherein $R_a$, $R_b$, and $R_c$ are alkyl.

In some cases, a photoisomerizable regulator present in a conjugate of the present disclosure is a non-permanently charged compound. In some cases, a photoisomerizable regulator present in a conjugate of the present disclosure comprises a substituted azobenzene group. In some cases, a photoisomerizable regulator present in a conjugate of the present disclosure is a cis blocker, e.g., blocks a receptor (such as an ion channel) when in the cis isomeric form. In other cases, a photoisomerizable regulator present in a conjugate of the present disclosure is a trans-blocker blocker, e.g., blocks a receptor (such as an ion channel) when in the trans isomeric form.

In some cases, a conjugate of the present disclosure binds to more than one polypeptide. For example, QAQ blocks voltage-gated potassium channels ($K_v$), voltage-gated sodium channels ($Na_v$), and voltage-gated calcium channels ($Ca_v$) channels. In other cases, a conjugate of the present disclosure exhibits selectivity, e.g., in some embodiments, a subject synthetic regular selectively blocks a voltage-gated potassium channel, but does not substantially block a voltage-gated sodium channel or a voltage-gated calcium channel.

In some cases, a photoisomerizable regulator present in a conjugate of the present disclosure comprises a red-shifted photoisomerizable group, e.g., the photoisomerizable group of a photoisomerizable regulator present in a conjugate of the present disclosure is in a first isomeric form when exposed to a first wavelength of light, and is in a second isomeric form when exposed to a second wavelength of light, where the second wavelength is shifted toward the red end of the spectrum compared to the first wavelength of light. As an example, DAAQ is in a first isomeric form at 472 nm and in a second isomeric form at 550 nm.

In some cases, a conjugate of the present disclosure is membrane permeant, e.g., will cross a eukaryotic cell membrane without the need for any additional physical, electrical, or chemical stimulus to be applied to the cell.

In some cases, a conjugate of the present disclosure is membrane impermeant; for example, in some cases, a conjugate of the present disclosure enters a eukaryotic cell only upon application of an additional physical, electrical, or chemical stimulus to the cell. For example, in some cases, a conjugate of the present disclosure enters a eukaryotic cell (e.g., a neuron) only upon application of a physical, electrical, or chemical stimulus that activates a nonselective ion channel. Nonselective ion channels include, e.g., ligand-gated nonselective cation channels. Nonselective cation channels include, e.g., $TRPV_1$, $P2X_7R$, and the like. $P2X_7R$ (or P2X purinoceptor 7) is described in, e.g., Chessell et al. (2005) *Pain* 114:386; and Rassendren et al. (1997) *J. Biol. Chem.* 272:5482. $P2X_7R$ can be activated by adenosine triphosphate (ATP), or an ATP analog. An example of a membrane-impermeant photoisomerizable regulator is QAQ.

$TRPV_1$ (transient receptor potential cation channel, subfamily V, member 1; also known as vanilloid receptor type 1), is a ligand-gated non-selective cation channel that is activated by a variety of endogenous and exogenous physical and chemical stimuli, including, e.g., heat over 43° C., low pH, the endocannabinoid anandamide, N-arachidonoyl-dopamine, and capsaicin. For $TRPV_1$, see, e.g., Cui et al. (2006) *J. Neurosci.* 26:9385.

$TRPV_1$ agonists include, e.g., capsaicin; a capsaicinoid (where capsaicinoids include, e.g., capsiate (4-hydroxy-3-methoxybenzyl (E)-8-methyl-6-nonenoate); dihydrocapsiate (4-hydroxy-3-methoxybenzyl 8-methylnonanoate); nordihydrocapsiate (4-hydroxy-3-methoxybenzyl 7-methyl-octanoate); capsiate derivatives such as vanillyl decanoate, vanillyl nonanoate, vanillyl octanoate and the like; fatty acid esters of vanillyl alcohol; and various straight chain or branched chain fatty acids which have a fatty acid chain length similar to that of nordihydrocapsiate); resiniferatoxin; olvanil; tinyatoxin; a compound as described in U.S. Patent Publication No. 2006/0240097; a compound as described in U.S. Patent Publication No. 2009/0203774; a pentadienamide derivative as described in U.S. Patent Publication No. 2009/0203667; a compound as described in U.S. Patent Publication No. 2009/0170942; and the like.

Exemplary compounds suitable for inclusion in a conjugate of the present disclosure include the following structures:

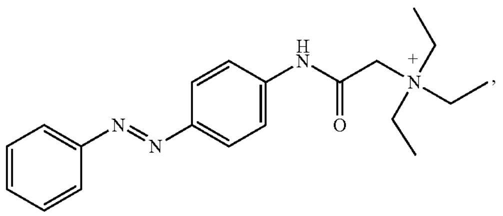
,

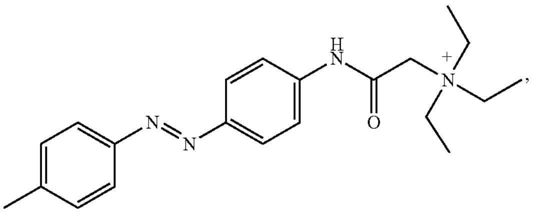
,

-continued

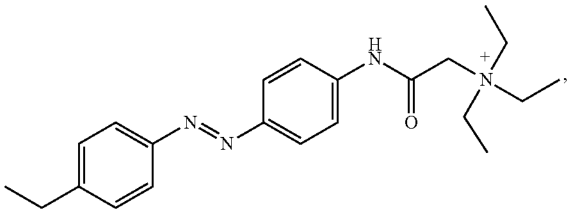
,

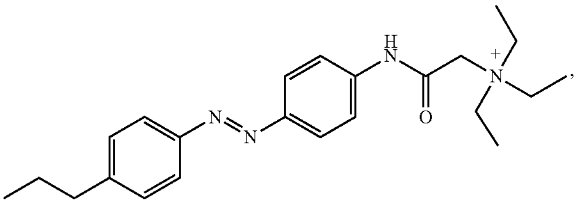
,

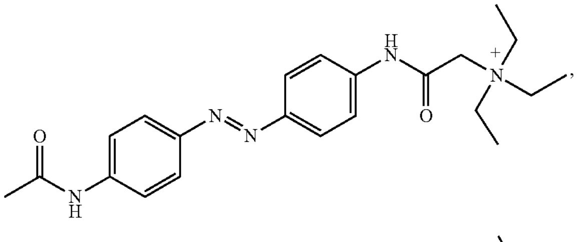
,

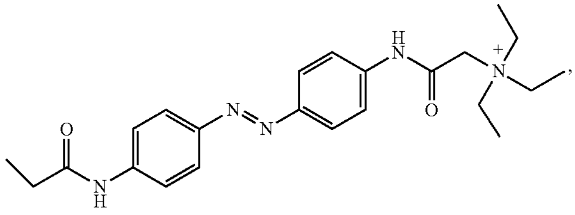
,

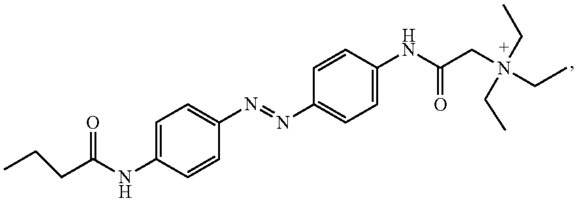
,

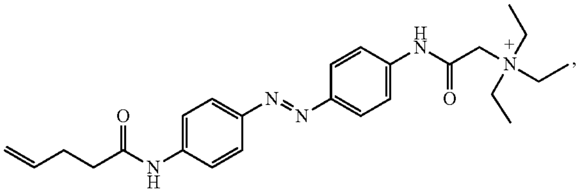
,

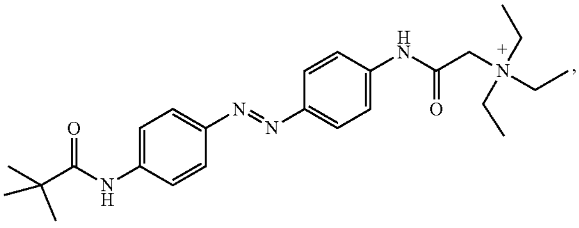
,

-continued
(BzAQ)
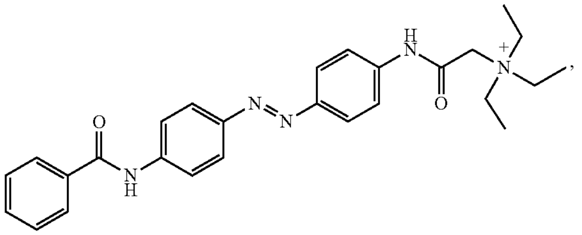
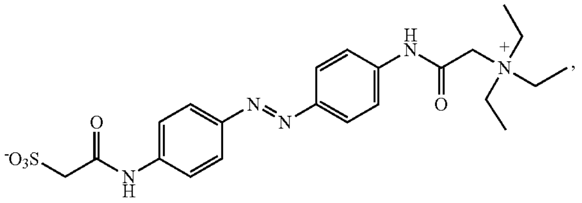
(QAQ)
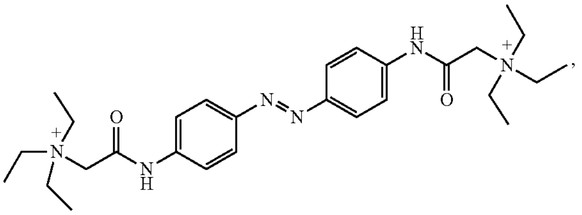
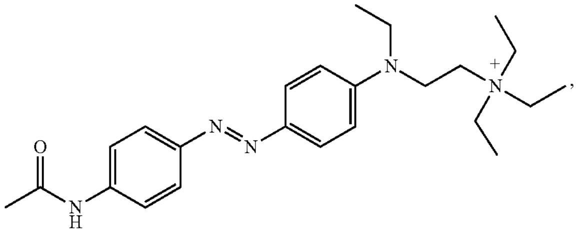
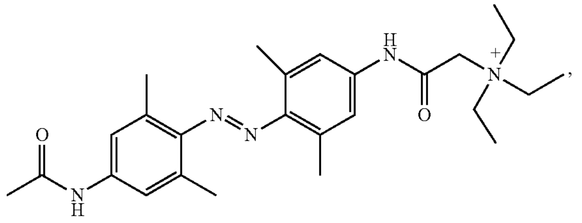
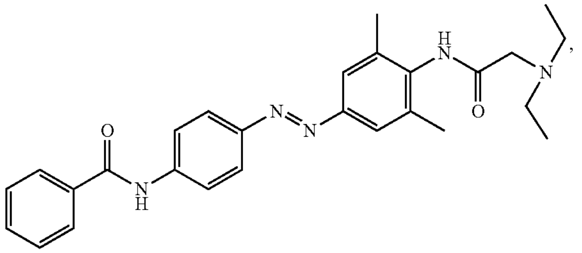
(BEAAQ)
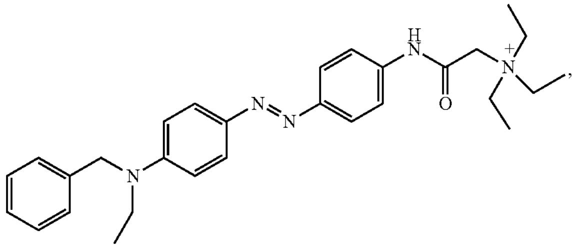
-continued
(DAAQ)
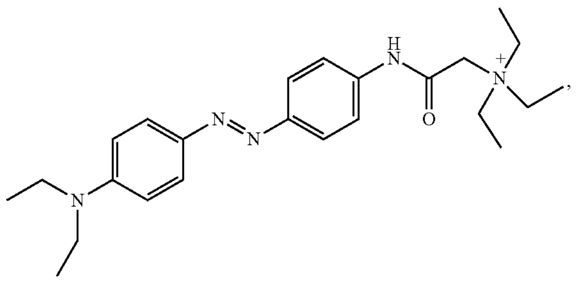
(7.72)
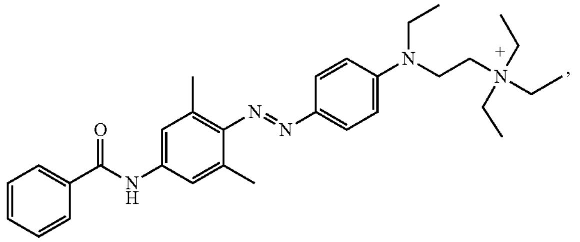
(7.73)
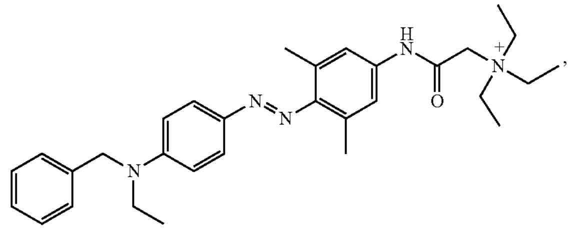
(7.75)
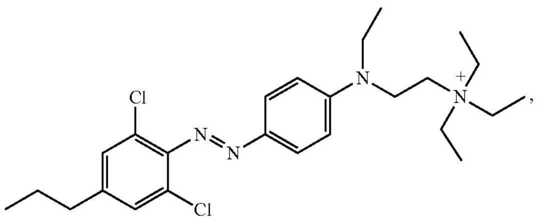
and
(7.76)
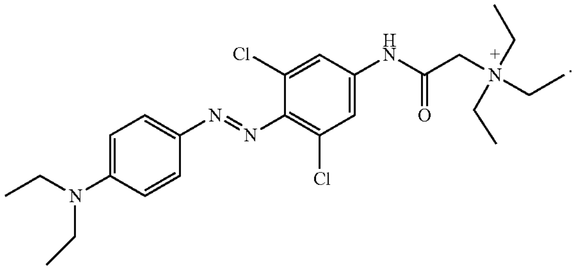

In some cases, the target polypeptide is a metabotropic glutamate receptor, such as mGluR2 or mGluR8 (which may be present in an amacrine cell) or mGluR6 or mGluR7 (which may be present in a bipolar cell) or mGluR4 (which may be present in a ganglion cell). In these cases, a suitable photo-isomerizable moiety-ligand combination is azobenzene-glutamate with a D stereoisomer linkage.

In some cases, the target polypeptide is an ionotropic glutamate receptor, such as GluK2, GluK5, GluN2A or GluN2B (which may be present in a bipolar, amacrine or ganglion cell). In these cases, a suitable photo-isomerizable moiety-ligand combination is azobenzene-glutamate with an L stereoisomer linkage.

In some cases, the target polypeptide is an ionotropic glutamate receptor, such as GluRA1. As one example, a suitable photo-isomerizable moiety-ligand combination is ShuBQX-3.

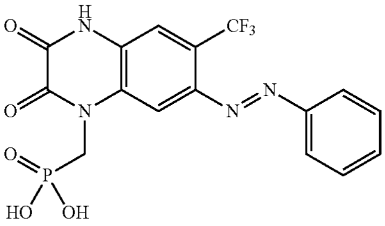

ShuBQX-3

In some cases, the target polypeptide is an ionotropic nicotinic acetylcholine receptor (which may be present in amacrine or ganglion cells) and the ligand is AC-5, MAACh, HoChPE, MG-624 or MAHoCh.

1

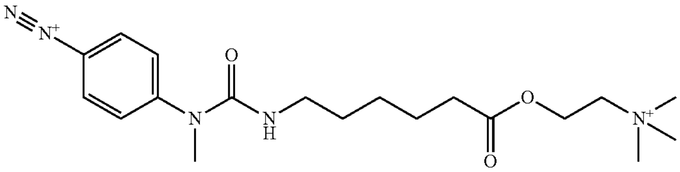

AC-5

4a

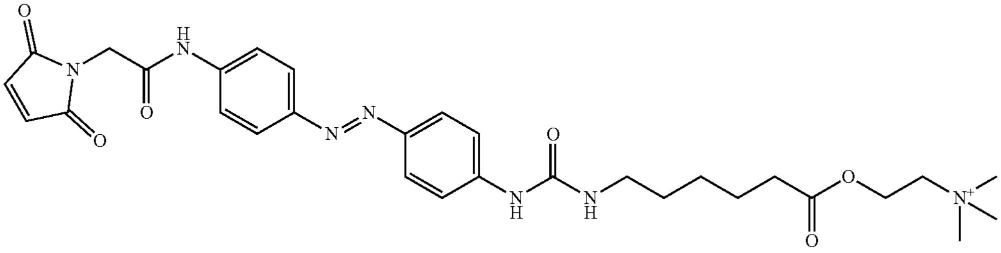

trans-MAACh

2

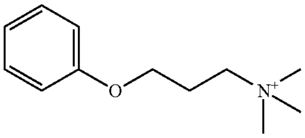

HoChPE

3

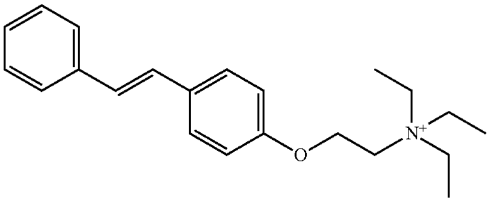

MG-624

-continued

5a

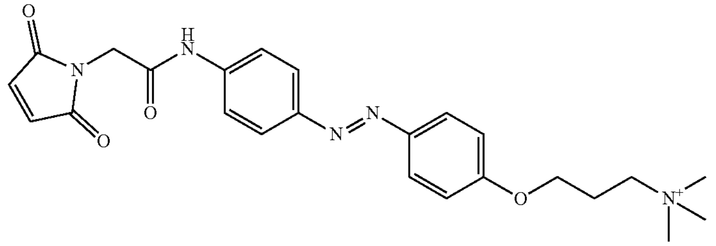

trans-MAHoCh

In some cases, the target polypeptide is an ionotropic GABA-A receptor (which may be present in amacrine cells or ganglion cells) and the ligand is PAG-2A, PAG-2B3, or PAG-3C.

In some cases, the target polypeptide is an ionotropic P2X receptor (which may be present in ganglion cells) and the ligand is MEA-TMA.

1a

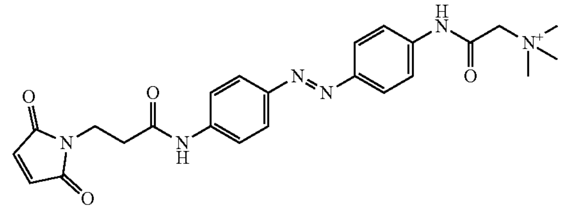

Trans
MEA-TMA

A conjugate of the present disclosure is useful for modulating an activity of a target ligand-binding polypeptide by use of light. A photoisomerizable regulator suitable for inclusion in a conjugate of the present disclosure can be provided in any number of configurations, including linear and branched, which can be affected by light.

For example, the configuration of BzAQ can change with application of certain wavelengths of light.

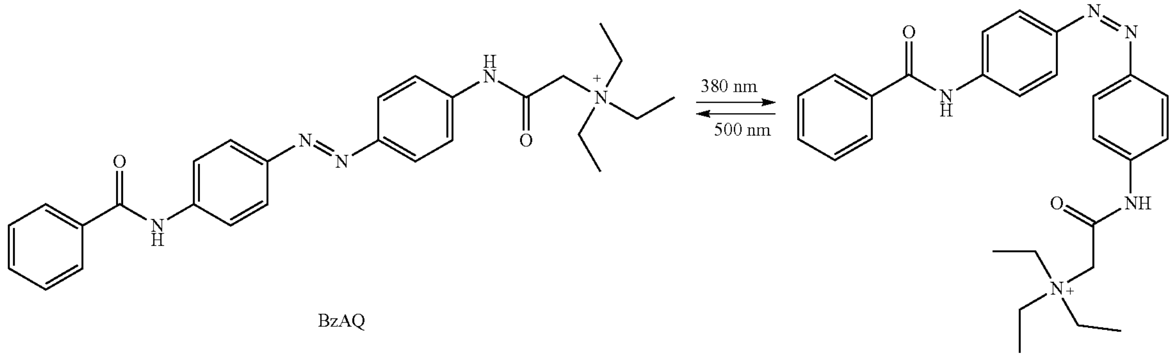

BzAQ

Other characteristics of BzAQ include being a trans-blocker, an external blocker, and selective for Kv channels.

In another example, the configuration of BEAAQ can change with application of certain wavelengths of light.

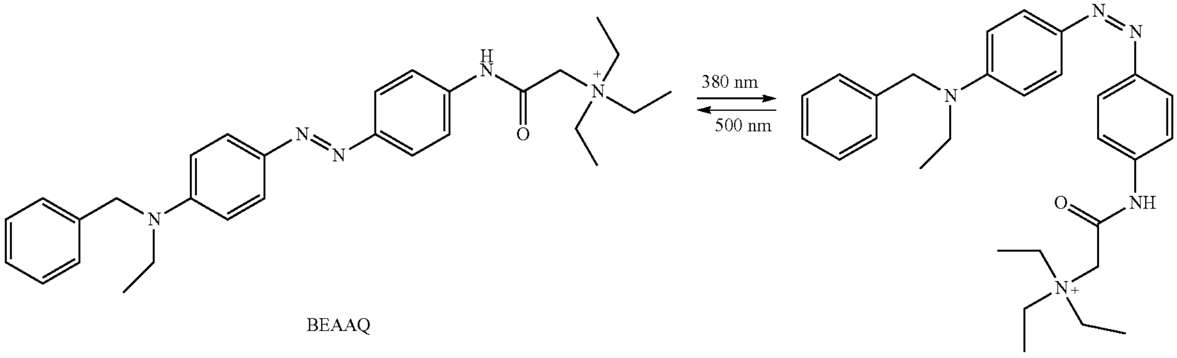

BEAAQ

Other characteristics of BEAAQ include being a cis-blocker and being able to block $K_v$ channels.

In another example, the configuration of DAAQ can change with application of certain wavelengths of light.

ion channel (e.g., potassium channels, chloride channels, sodium channels, and the like); an acetylcholine receptor; a nicotinic acetylcholine receptor; a muscarinic acetylcholine receptor; a capsaicin receptor; a serotonin receptor; a cap-

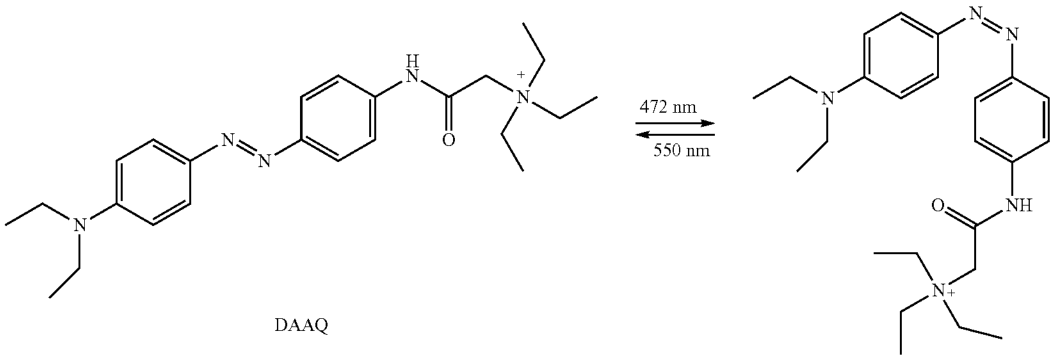

DAAQ

Other characteristics of DAAQ include being a trans-blocker, an external blocker, a red-shifted compound, and being able to block $K_v$ channels.

In another example, the configuration of QAQ can change with application of certain wavelengths of light.

saicin receptor; and the like. Suitable ion channels voltage regulated ion channels, cAMP regulated ion channels, and ligand gated ion channels.

Coupling an Affinity Agent to a Photoisomerizable Regulator

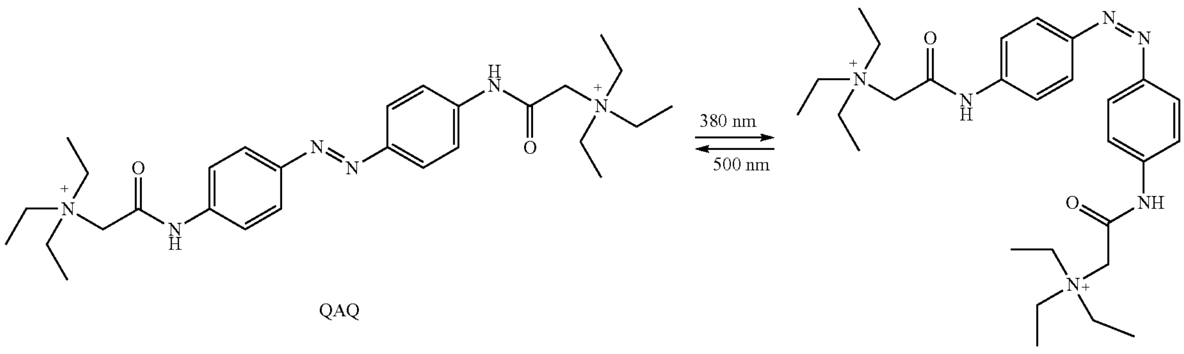

QAQ

Other characteristics of QAQ include being a trans-blocker, an internal blocker, and being able to block Kv, Nav, and Cav channels.

Target Ligand-Binding Polypeptides

Suitable target ligand-binding polypeptides include any of a variety of polypeptides that bind a ligand. Suitable target ligand-binding polypeptides include, but are not limited to, An affinity agent can be coupled (e.g., covalently linked to) a photoisomerizable regulator using any of a variety of well-known chemistries. An affinity agent can be coupled (e.g., covalently linked to) a photoisomerizable regulator directly or via a linker.

Where the affinity agent is a polypeptide (e.g., an antibody), the affinity agent can be coupled (e.g., covalently linked to) a photoisomerizable regulator by use of a HALO-tag, a SNAP tag, a CLIP tag, a lumio tag, and the like. For example, a nucleic acid comprising a nucleotide sequence encoding a SNAP tag fused in-frame to a single chain antibody, a single-domain antibody, or a nanobody is introduced into a cell for production of the SNAP-antibody fusion protein. The SNAP-antibody fusion protein is then combined with a photoisomerizable regulator, where the photoisomerizable regulator is linked to the SNAP-antibody fusion protein via the SNAP tag. Thus, in some cases, an affinity agent suitable for inclusion in a conjugate of the present disclosure is a SNAP tag-antibody fusion polypeptide. In some cases, an affinity agent suitable for inclusion in a conjugate of the present disclosure is a HALO tag-antibody fusion polypeptide. In some cases, an affinity agent suitable for inclusion in a conjugate of the present disclosure is a CLIP tag-antibody fusion polypeptide.

A SNAP tag can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

```
                                             (SEQ ID NO: 1)
MDKDCEMKRTTLDSPLGKLELSGCEQGLHRIIFLGKGTSAADAVEVPAP

AAVLGGPEPLMQATAWLNAYFHQPEAIEEFPVPALHHPVFQQESFTRQV

LWKLLKVVKFGEVISYSHLAALAGNPAATAAVKTALSGNPVPILIPCHR

VVQGDLDVGGYEGGLAVKEWLLAHEGHRLGKPGLG.

A SNAP tag binds benzylguanine.
```

A HALO tag can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

```
                                             (SEQ ID NO: 2)
MAEIGTGFPFDPHYVEVLGERMHYVDVGPRDGTPVLFLHGNPTSSYVWR

NIIPHVAPTHRCIAPDLIGMGKSDKPDLGYFFDDHVRFMDAFIEALGLE

EVVLVIHDWGSALGFHWAKRNPERVKGIAFMEFIRPIPTWDEWPEFARE

TFQAFRTTDVGRKLIIDQNVFIEGTLPMGVVRPLTEVEMDHYREPFLNP

VDREPLWRFPNELPIAGEPANIVALVEEYMDWLHQSPVPKLLFWGTPGV

LIPPAEAARLAKSLPNCKAVDIGPGLNLLQEDNPDLIGSEIARWLSTLE

ISG. A HALO tag binds chloroalkane.
```

A CLIP tag can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino

```
                                             (SEQ ID NO: 3)
MDKDCEMKRTTLDSPLGKLELSGCEQGLHRIIFLGKGTSAADAVEVPAP

AAVLGGPEPLIQATAWLNAYFHQPEAIEEFPVPALHHPVFQQESFTRQV
```

-continued

```
LWKLLKVVKFGEVISESHLAALVGNPAATAAVNTALDGNPVPILIPCHR

VVQGDSDVGPYLGGLAVKEWLLAHEGHRLGKPGLG.

A CLIP tag can bind benzylcytosine.
```

In some cases, the coupling is via an amino acid side chain in a polypeptide affinity agent. Linkage of the photoisomerizable regulator to a polypeptide affinity agent can be via a tyrosine residue, a tryptophan residue, a serine residue, a threonine residue, cysteine residue, a histidine residue, an arginine residue, a lysine residue, an aspartic acid residue, a glutamic acid residue, or any natural or unnatural amino acid in the polypeptide affinity agent that is accessible for reacting with a binding moiety present in the photoisomerizable regulator. Suitable binding moieties include, but are not limited to, a maleimide, an acrylic ester, an acrylic amide (an acrylamide), an α-haloacetamide, an epoxide, an O-succinimidyl ester, a disulfide, and a methanethiosulfonate compound. In some cases, the binding moiety is other than a bromomethyl moiety; e.g., in some cases, a bromomethyl moiety is specifically excluded. For examples of covalent linkage to an amino acid residue see e.g. Hermanson (1996) Bioconjugate Techniques, Academic Press.

Where the amino acid to which the photoisomerizable regulator is to be linked is a cysteine residue, the photoisomerizable regulator can comprise a moiety such as, e.g., a vinylsulfone group, maleimide; a substituted maleimide, such as maleic anhydride; orthopyridyl-disulfide; a methanethiosulfonate; a disulfide; and the like. Where the amino acid to which the photoisomerizable regulator is to be linked is a lysine residue, the photoisomerizable regulator can comprise a moiety such as, e.g., carbodiimide EDC (1-(3-dimethylaminopropyl)-3-ethylcarbodiimide hydrochloride). Where the amino acid to which the photoisomerizable regulator is to be linked is an arginine residue, the photoisomerizable regulator can comprise, e.g., 2,3-butanedione, phenylglyoxal, or glyoxal.

For example, cysteinyl residues most commonly are reacted with α-haloacetates (and corresponding amides), such as chloroacetic acid or chloroacetamide, to give carboxymethyl or carboxyamidomethyl derivatives. Cysteinyl residues also are reacted with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are reacted with diethylpyrocarbonate at pH 5.5-7.0 because this agent is relatively specific for the histidyl side chain. Parabromophenacyl bromide also is useful; the reaction is generally performed in 0.1 M sodium cacodylate at pH 6.0. Lysinyl and amino terminal residues are reacted with succinic acid or other carboxylic acid anhydrides. Other suitable reagents for reacting with α-amino-containing residues include imidoesters such as methyl picolinimidate; pyridoxal phosphate; pyridoxal; chloroborohydride; trinitrobenzenesulfonic acid; O-methylisourea; and 2,4-pentanedione. Arginyl residues are reacted with one or several conventional reagents, among them phenylglyoxal, 2,3-butanedione, or 1,2-cyclohexanedione. Carboxyl side groups (aspartyl or glutamyl) are reacted with carbodiimides (R—N═C═N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide.

The photoisomerizable regulator can include an alkylating agent, acylating agent, ketone, aldehyde, sulphonate or a phosphorylating agent. Examples of particular binding moieties include, but are not limited to fluorophosphonyl, fluorophosphoryl, fluorosulfonyl, alpha-haloketones or aldehydes or their ketals or acetals, respectively, alpha-haloacyls, nitriles, sulfonated alkyl or aryl thiols, iodoacetylamide group, maleimides, sulfonyl halides and esters, isocyanates, isothiocyanantes, tetrafluorophenyl esters, N-hydroxysuccinimidyl esters, acid halides, acid anhydrides, unsaturated carbonyls, alkynes, hydroxamates, alpha-halomethylhydroxamates, aziridines, epoxides, or arsenates and their oxides. Suitable sulfonyl groups include sulfonates, sulfates, sulfinates, sulfamates, etc., in effect, any reactive functionality having a sulfur group bonded to two oxygen atoms. Suitable epoxides include aliphatic, aralkyl, cycloaliphatic and spiro epoxides.

Compositions

The embodiments further provide compositions comprising an affinity-tagged photoswitch of the present disclosure. Compositions comprising a conjugate of the present disclosure can include one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-morpholino)ethanesulfonic acid (MES), 2-(N-morpholino)ethanesulfonic acid sodium salt (MES), 3-(N-Morpholino)propanesulfonic acid (MOPS), N-tris[hydroxymethyl]methyl-3-aminopropanesulfonic acid (TAPS), etc.; a solubilizing agent; a detergent, e.g., a non-ionic detergent such as Tween-20, Nonidet-P40, etc.; a protease inhibitor; and the like.

Pharmaceutical Compositions

The embodiments provide pharmaceutical compositions comprising a conjugate of the present disclosure. In some cases, the pharmaceutical composition is suitable for administering to an individual in need thereof. In some cases, the pharmaceutical composition is suitable for administering to an individual in need thereof, where the individual is a human.

A pharmaceutical composition comprising a conjugate of the present disclosure may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A pharmaceutical composition comprising a conjugate of the present disclosure can optionally include a pharmaceutically acceptable carrier(s) that facilitate processing of an active ingredient into pharmaceutically acceptable compositions. As used herein, the term "pharmacologically acceptable carrier" refers to any carrier that has substantially no long-term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in "Pharmaceutical Dosage Forms and Drug Delivery Systems" (Howard C. Ansel et al., eds., Lippincott Williams & Wilkins Publishers, 7$^{th}$ ed. 1999); "Remington: The Science and Practice of Pharmacy" (Alfonso R. Gennaro ed., Lippincott, Williams & Wilkins, 20$^{th}$ 2000); "Goodman & Gilman's The Pharmacological Basis of Therapeutics" Joel G. Hardman et al., eds., McGraw-Hill Professional, 10.sup.th ed. 2001); and "Handbook of Pharmaceutical Excipients" (Raymond C. Rowe et al., APhA Publications, 4$^{th}$ edition 2003).

A subject pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a subject pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a subject pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A conjugate of the present disclosure can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In a method of the present disclosure (described below), a conjugate of the present disclosure may be administered to the host using any convenient means capable of resulting in the desired reduction in disease condition or symptom. Thus, a conjugate of the present disclosure can be incorporated into a variety of formulations for therapeutic administration. More particularly, a conjugate of the present disclosure can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

A conjugate of the present disclosure can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A conjugate of the present disclosure can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some cases, a composition of the present disclosure, comprising a conjugate of the present disclosure, is administered via intravitreal injection. In some cases, a composition of the present disclosure, comprising a conjugate of the present disclosure, is administered via intraocular administration. In some cases, a composition of the present disclosure, comprising a conjugate of the present disclosure, is administered via subretinal injection.

A conjugate of the present disclosure can be utilized in aerosol formulation to be administered via inhalation. A conjugate of the present disclosure can be formulated into pressurized acceptable propellants such as dichlorodifluoromethane, propane, nitrogen and the like.

Furthermore, a conjugate of the present disclosure can be made into suppositories by mixing with a variety of bases such as emulsifying bases or water-soluble bases. A conjugate of the present disclosure can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a conjugate of the present disclosure in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a conjugate of the present disclosure calculated in an amount sufficient to produce the desired effect in association with a pharmaceutically acceptable diluent, carrier or vehicle. The specifications for a conjugate of the present disclosure depend on the particular compound employed and the effect to be achieved, and the pharmacodynamics associated with each compound in the host.

A conjugate of the present disclosure can be administered as injectables. Injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some cases, a conjugate of the present disclosure is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Methods

A conjugate of the present disclosure finds use in modulating activity of a target ligand-binding polypeptide. A conjugate of the present disclosure finds use in modulating activity of a cell comprising a conjugate of the present disclosure, where the cell comprises a target ligand-binding polypeptide. The present disclosure thus provides a method of modulating activity of a target ligand-binding polypeptide; and a method of modulating activity of a cell comprising a conjugate of the present disclosure, where the cell comprises a target ligand-binding polypeptide. In some cases, a method of the present disclosure comprises exposing the conjugate (or a cell or tissue comprising the conjugate) to appropriate light conditions such that the ligand binds to the ligand-binding site of the target ligand-binding polypeptide. In some cases, a method of the present disclosure comprises exposing the conjugate (or a cell or tissue comprising the conjugate) to appropriate light conditions such that the ligand does not bind to the ligand-binding site of the target ligand-binding polypeptide.

The present disclosure provides a method of modulating activity of a target ligand-binding polypeptide, the method comprising: a) contacting the target ligand-binding polypeptide with a conjugate of the present disclosure, generating a light-regulatable polypeptide; and b) exposing the light-regulatable polypeptide to light of a wavelength that results in binding of the ligand to the light-regulatable polypeptide, wherein binding of the ligand to the light-regulatable polypeptide modulates activity of the light-regulatable polypeptide. The present disclosure provides a method of modulating activity of a target ligand-binding polypeptide, the method comprising: a) contacting the target ligand-binding polypeptide with a conjugate of the present disclosure, generating a light-regulatable polypeptide; and b) exposing the light-regulatable polypeptide to light of a wavelength that results in release of the ligand from the ligand-binding site of the light-regulatable polypeptide, wherein release of the ligand from the ligand-binding site of the light-regulatable polypeptide modulates activity of the light-regulatable polypeptide.

"Modulating activity" of a target ligand-binding polypeptide (or a light-regulatable polypeptide) includes increasing an activity of the polypeptide; inhibiting an activity of the polypeptide; sensitizing the polypeptide to another (e.g., non-light) stimulus); reducing the sensitivity of the polypeptide to another stimulus; increasing the efficacy by which another stimulus activates the polypeptide; and decreasing the efficacy by which another stimulus activates the polypeptide. The activity depends on the polypeptide being modulated. For example, in some cases, the ligand is an agonist, and binding of the ligand to the target ligand-binding polypeptide (or light-regulatable polypeptide) results in activation of the target ligand-binding polypeptide (or light-regulatable polypeptide). In other instances, the ligand is an antagonist, and binding of the ligand to the target ligand-binding polypeptide (or light-regulatable polypeptide) results in inhibition, desensitization, or inactivation of the target ligand-binding polypeptide (or light-regulatable polypeptide).

Target ligand-binding polypeptides include, but are not limited to, a transcription regulator, an ion channel, a cation channel, a ligand-gated ion channel, a voltage-gated ion channel, a quorum sensor, a pheromone receptor, a neurotransmitter receptor, an enzyme, enzyme, a motor protein, a transporter, a membrane transport protein, a G protein-coupled receptor, a G protein, a receptor tyrosine kinase, a scaffolding protein, an adaptor protein, a cytoskeletal protein, an adhesion protein, a membrane-targeting protein, a protein that direct secretion, and a localization or protein interaction domain of a protein. In some cases, the target ligand-binding polypeptide is a cation channel. In some cases, the target ligand-binding polypeptide is an anion channel. In some cases, the target ligand-binding polypeptide is a potassium channel. In some cases, the target ligand-binding polypeptide is a sodium channel. In some cases, the target ligand-binding polypeptide is a calcium channel.

In some cases, the target ligand-binding polypeptide is in a cell-free composition; i.e., the target ligand-binding polypeptide is not present in a cell.

In some cases, the target ligand-binding polypeptide is present in a cell in vitro. In some cases, the target ligand-binding polypeptide is present in a cell in vivo.

Where the target ligand-binding polypeptide is present in a cell, the cell can be any type of cell. For example, the cell can be a mammalian cell, e.g., a human cell, a non-human primate cell, a rodent cell, and the like. The cell can be a retinal cell, a muscle cell, a neuronal cell, a blood cell (e.g., a nucleated blood cell), an epithelial cell, an endothelial cell, a skin cell, a lung cell, etc.

In some cases, the target ligand-binding polypeptide is present in a cell. In some cases, the cell is a retinal cell. In some cases, the cell is an amacrine cell. In some cases, the cell is a ganglion cell. In some cases, the cell is a bipolar cell. In some cases, the cell is a Mueller cell.

The present disclosure provides a method of modulating activity of a target cell, the method comprising exposing the target cell to light, where the target cell comprises a conjugate of the present disclosure and a target ligand-binding polypeptide, where the light is of a wavelength that results in binding of the ligand to the target ligand-binding polypeptide, and where binding of the ligand to the target ligand-binding polypeptide modulates activity of the target cell. The present disclosure provides a method of modulating activity of a target cell, the method comprising exposing the target cell to light, where the target cell comprises a conjugate of the present disclosure and a target ligand-binding polypeptide, where the light is of a wavelength that results in release of the ligand from the target ligand-binding polypeptide, and where release of binding of the ligand from the target ligand-binding polypeptide modulates activity of the target cell. In some cases, the cell is a target cell population. In some cases, the target cell or cell population is present in a tissue.

The present disclosure provides a method of introducing sensitivity to light into retinal cells that normally are not directly responsive to light or enhancing the light response of already light-sensitive retinal cells, the method comprising exposing the retinal cell to light, wherein the retinal cell comprises a conjugate of the present disclosure and a target ligand-binding polypeptide, where the light is of a wavelength that results in binding of the ligand to the target ligand-binding polypeptide, and where binding of the ligand to the target ligand-binding polypeptide modulates the activity of the retinal cell in response to light. For example, the target polypeptide in the retinal cell may be a metabotropic glutamate receptor, such as mGluR2 or mGluR8 in amacrine cells or mGluR6 or mGluR7 in bipolar cells or mGluR4 in ganglion cells. In these cases a suitable photo-isomerizable moiety-ligand combination could be azobenzene-glutamate with a D stereoisomer linkage. See, e.g., Broichhagen et al. (2015) *ACS Central Science* 1, 383-393; and Levitz et al. (2017) *Proc. Natl. Acad. Sci. USA* 114, E3546-E3554. As other examples, the target polypeptide may be an ionotropic glutamate receptor, such as GluK2, GluK5, GluN2A or GluN2B in bipolar, amacrine or ganglion cells. In these cases, a suitable photo-isomerizable moiety-ligand combination could be azobenzene-glutamate with an L stereoisomer linkage (see, e.g., Volgraf et al. (2006) *Nature Chem. Bio.* 2:47; Volgraf et al. (2007) *J. Am. Chem. Soc.* 129:260; and Berlin et al. (2016) *Elife* 5:e12040), or ATG (see, e.g., Laprell et al. (2015) *Nat. Commun.* 6:8076. As another example, the target polypeptide may be an ionotropic glutamate receptor, such as GluRA1. In this case, a suitable photo-isomerizable moiety-ligand combination could be ShuBQX-3 (see, e.g., Barber et al. (2017) *Chem. Sci.* 8:611). As another example, the target polypeptide may be an ionotropic nicotinic acetylcholine receptor in amacrine or ganglion cells and the ligand may be AC-5, MAACh, HoChPE, MG-624 or MAHoCh (see, e.g., Tochitsky et al. (2012) *Nat. Chem.* 4:105. As another example, the target polypeptide may be an ionotropic GABA-A receptor in amacrine cells or ganglion cells and the ligand may be PAG-2A, PAG-2B, or PAG-3C. As another example, the target polypeptide may be an ionotropic P2X receptor in ganglion cells and the ligand may be MEA-TMA (see, e.g., Lemoine et al. (2013) *Proc. Natl. Acad. Sci. USA* 110:20813.

The present disclosure provides method of treating an ocular disorder characterized by reduced responsiveness to light, the method comprising administering a conjugate of the present disclosure, or a composition (e.g., a pharmaceutical composition) comprising a conjugate of the present disclosure, to an eye of an individual having the ocular disorder. In some cases, the conjugate, or a composition (e.g., a pharmaceutical composition) comprising the conjugate, is administered to the individual via intravitreal injection. In some cases, the conjugate, or a composition (e.g., a pharmaceutical composition) comprising the conjugate, is administered to the individual via intraocular administration. In some cases, the conjugate, or a composition (e.g., a pharmaceutical composition) comprising the conjugate, is administered to the individual via subretinal injection.

Ocular disorders characterized by reduced responsiveness to light include, but are not limited to, inherited retinal degenerative diseases such as retinitis pigmentosa and age-related macular degeneration. Ocular disorders that are suitable for treatment with a method of the present disclosure include, but are not limited to, retinitis pigmentosa, macular degeneration, retinoschisis, and Leber's Congenital Amaurosis, and diabetic retinopathy.

Cells Comprising Fusion Polypeptide Comprising Photoswitch Anchoring Domain and an Affinity Agent The present disclosure provides a method of modulating activity of a target polypeptide, the method comprising: a) contacting a cell comprising the target polypeptide with a photoisomerizable regulator comprising i) a photoisomerizable group; and ii) a ligand that binds to the target ligand-binding polypeptide, where the cell is genetically modified with a nucleic acid comprising a nucleotide sequence encoding an affinity agent that specifically binds to an epitope presented by the target polypeptide, where the affinity agent comprises a moiety that provides for attachment of the photoisomerizable regulator within the cell. For example, the affinity agent can comprise: i) a photoswitch anchoring domain (e.g., a HALO-tag, a SNAP-tag, or a CLIP-tag); ii) a non-naturally occurring amino acid; iii) an amino acid sequence comprising a single cysteine residue, e.g., for attachment of a thiol-reactive photoswitch. In some cases, the method comprises the step of introducing into the cell a nucleic acid comprising a nucleotide sequence encoding an affinity agent that specifically binds to an epitope presented by the target polypeptide.

The present disclosure provides a method of modulating activity of a target polypeptide, the method comprising: a) contacting a cell comprising the target polypeptide with a photoisomerizable regulator comprising i) a photoisomerizable group; and ii) a ligand that binds to the target ligand-binding polypeptide, where the cell comprises an affinity agent that specifically binds to an epitope presented by the target polypeptide, where the affinity agent comprises a moiety that provides for attachment of the photoisomerizable regulator within the cell. For example, the affinity agent can comprise: i) a photoswitch anchoring domain (e.g., a HALO-tag, a SNAP-tag, or a CLIP-tag); ii) a non-naturally occurring amino acid; iii) an amino acid sequence comprising a single cysteine residue, e.g., for attachment of a thiol-reactive photoswitch. In some cases, the affinity agent is introduced into the cell as a polypeptide per se.

The present disclosure provides a method of modulating activity of a target polypeptide, the method comprising: a) contacting a cell comprising the target polypeptide with a photoisomerizable regulator comprising i) a photoisomerizable group; and ii) a ligand that binds to the target ligand-binding polypeptide, where the cell is genetically modified with a nucleic acid comprising a nucleotide sequence encoding a fusion polypeptide comprising: i) an affinity agent that specifically binds to an epitope presented by the target polypeptide; and ii) photoswitch anchoring domain (e.g., a HALO-tag, a SNAP-tag, or a CLIP-tag), wherein the fusion polypeptide forms a conjugate with the photoisomerizable regulator, wherein the affinity agent present in the conjugate binds to the target polypeptide, forming a light-regulatable polypeptide; and b) exposing the light-regulatable polypeptide to light of a wavelength that results in binding of the ligand to the light-regulatable polypeptide, and wherein binding of the ligand to the light-regulatable polypeptide modulates activity of the light-regulatable polypeptide. Suitable photoisomerizable regulators are described above. For example, any of the above-described photoisomerizable regulators (not conjugated to an affinity agent) can be used. In some cases, the method comprises the step of introducing into the cell a nucleic acid comprising a nucleotide sequence encoding an affinity agent that specifically binds to an epitope presented by the target polypeptide.

In some cases, a method of the present disclosure comprises exposing the a cell or tissue comprising the target polypeptide (where the cell is genetically modified to comprise a nucleic acid comprising a nucleotide sequence encoding a fusion polypeptide comprising: i) an affinity agent that specifically binds to an epitope presented by the target polypeptide; and ii) photoswitch anchoring domain (e.g., a HALO-tag, a SNAP-tag, or a CLIP-tag)) to appropriate light conditions such that the ligand does not bind to the ligand-binding site of the target ligand-binding polypeptide.

For example, in some cases, the cell is contacted with a photoisomerizable regulator that comprises a benzylguanine moiety (for covalent binding to a SNAP tag, where the target cell is genetically modified with a nucleic acid comprising a nucleotide sequence encoding a fusion polypeptide comprising: i) an affinity agent; and ii) a SNAP tag). As another example, in some cases, the cell is contacted with a photoisomerizable regulator that comprises a chloroalkane moiety (for covalent binding to a HALO tag, where the target cell is genetically modified with a nucleic acid comprising a nucleotide sequence encoding a fusion polypeptide comprising: i) an affinity agent; and ii) a HALO tag). As another example, in some cases, the cell is contacted with a photoisomerizable regulator that comprises a benzylcytosine moiety (for covalent binding to a CLIP tag, where the target cell is genetically modified with a nucleic acid comprising a nucleotide sequence encoding a fusion polypeptide comprising: i) an affinity agent; and ii) a CLIP tag).

In some cases, a target cell is genetically modified with a nucleic acid comprising a nucleotide sequence encoding a fusion polypeptide comprising: i) an affinity agent; and ii) a SNAP tag, a HALO tag, or a CLIP tag. In some cases, the affinity agent is an antibody. In some cases, the affinity agent is a nanobody. In some cases, the affinity agent is a scFv. In some cases, the fusion polypeptide comprises, in order from N-terminus to C-terminus: i) an affinity agent; and ii) an anchoring domain (a SNAP tag, a HALO tag, or a CLIP tag). In some cases, the affinity agent is a scFv. In some cases, the fusion polypeptide comprises, in order from N-terminus to C-terminus: i) an affinity agent; ii) a peptide linker of from about 1 amino acid to about 25 amino acids; and iii) an anchoring domain (a SNAP tag, a HALO tag, or a CLIP tag). In some cases, the fusion polypeptide comprises, in order from N-terminus to C-terminus: i) an anchoring domain (a SNAP tag, a HALO tag, or a CLIP tag); and ii) an affinity agent. In some cases, the fusion polypeptide comprises, in order from N-terminus to C-terminus: i) an anchoring domain (a SNAP tag, a HALO tag, or a CLIP tag); ii) a peptide linker of from about 1 amino acid to about 25 amino acids (or more than 25 amino acids) in length; and iii) an affinity agent. For example, a peptide linker can have a length of from 1 amino acid (aa) to 5 aa, from 5 aa to 10 aa, from 10 aa to 15 aa, from 15 aa to 20 aa, from 20 aa to 25 aa, from 25 aa to 50 aa, from 50 aa to 100 aa, from 100 aa to 150 aa, from 150 aa to 200 aa, or more than 200 aa.

A SNAP tag can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(SEQ ID NO: 1)
MDKDCEMKRTTLDSPLGKLELSGCEQGLHRIIFLGKGTSAADAVEVPAP

AAVLGGPEPLMQATAWLNAYFHQPEAIEEFPVPALHHPVFQQESFTRQV

LWKLLKVVKFGEVISYSHLAALAGNPAATAAVKTALSGNPVPILIPCHR

VVQGDLDVGGYEGGLAVKEWLLAHEGHRLGKPGLG.

A SNAP tag binds benzylguanine.

A HALO tag can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

(SEQ ID NO: 2)
MAEIGTGFPFDPHYVEVLGERMHYVDVGPRDGTPVLFLHGNPTSSYVWR

NIIPHVAPTHRCIAPDLIGMGKSDKPDLGYFFDDHVRFMDAFIEALGLE

EVVLVIHDWGSALGFHWAKRNPERVKGIAFMEFIRPIPTWDEWPEFARE

TFQAFRTTDVGRKLIIDQNVFIEGTLPMGVVRPLTEVEMDHYREPFLNP

VDREPLWRFPNELPIAGEPANIVALVEEYMDWLHQSPVPKLLFWGTPGV

LIPPAEAARLAKSLPNCKAVDIGPGLNLLQEDNPDLIGSEIARWLSTLE

ISG. A HALO tag binds chloroalkane.

A CLIP tag can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino (SEQ ID NO: 3)
MDKDCEMKRTTLDSPLGKLELSGCEQGLHRIIFLGKGTSAADAVEVPAP

AAVLGGPEPLIQATAWLNAYFHQPEAIEEFPVPALHHPVFQQESFTRQV

LWKLLKVVKFGEVISESHLAALVGNPAATAAVNTALDGNPVPILIPCHR

VVQGDSDVGPYLGGLAVKEWLLAHEGHRLGKPGLG.

A CLIP tag can bind benzylcytosine.

In some cases, a nucleic acid comprising a nucleotide sequence encoding a fusion polypeptide comprising: i) an affinity agent; and ii) an anchoring polypeptide (e.g., a SNAP tag, a HALO tag, or a CLIP tag) is present in a recombinant expression vector. Suitable expression vectors include, but are not limited to, a lentivirus vector, a herpes simplex virus (HSV) vector, an adenovirus vector, a retroviral vector, an adenoassociated virus (AAV) vector, and the like. Thus, in some cases, a nucleic acid comprising a nucleotide sequence encoding an anchoring polypeptide is a recombinant lentivirus vector, a recombinant HSV vector, a recombinant adenovirus vector, a recombinant retrovirus vector, or a recombinant AAV vector.

In some cases, the nucleotide sequence is operably linked to a promoter that provides for expression in a retinal cell. In some cases, the nucleotide sequence is operably linked to a promoter that generally provides for expression in a eukaryotic or mammalian cell.

Suitable promoters include, but are not limited to, a CAG promoter (Miyazaki et al. (1989) Gene 79:269); a synapsin promoter; a cytomegalovirus (CMV) promoter; a glutamate metabotropic receptor-6 (grm6) promoter (Cronin et al. (2014) *EMBO Mol. Med.* 6:1175); a Pleiades promoter (Portales-Casamar et al. (2010) *Proc. Natl. Acad. Sci. USA* 107:16589); a choline acetyltransferase (ChAT) promoter (Misawa et al. (1992) *J. Biol. Chem.* 267:20392); a vesicular glutamate transporter (V-glut) promoter (Zhang et al. (2011) *Brain Res.* 1377:1); a glutamic acid decarboxylase (GAD) promoter (Rasmussen et al. (2007) *Brain Res.* 1144:19; Ritter et al. (2016) *J. Gene Med.* 18:27); a cholecystokinin (CCK) promoter (Ritter et al. (2016) *J. Gene Med.* 18:27); a parvalbumin (PV) promoter; a somatostatin (SST) promoter; a neuropeptide Y (NPY) promoter; and a vasoactive intestinal peptide (VIP) promoter. Suitable promoters include, but are not limited to, a red cone opsin promoter, rhodopsin promoter, a rhodopsin kinase promoter, and a GluR promoter (e.g., a GluR6 promoter). Suitable promoters include, but are not limited to, a vitelliform macular dystrophy 2 (VMD2) gene promoter, and an interphotoreceptor retinoid-binding protein (IRBP) gene promoter. Also suitable for use is an L7 promoter (Oberdick et al. (1990) *Science* 248:223), a thy-1 promoter, a recoverin promoter (Wiechmann and Howard (2003) *Curr. Eye Res.* 26:25); a calbindin promoter; and a beta-actin promoter.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-55 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A conjugate comprising: a) an affinity agent that specifically binds a target ligand-binding polypeptide; b) a linker; and c) a photoisomerizable regulator comprising: i) a photoisomerizable group; and ii) a ligand that binds to the target ligand-binding polypeptide.

Aspect 2. The conjugate of aspect 1, wherein the affinity agent is an antibody.

Aspect 3. The conjugate of aspect 1, wherein the affinity agent is an aptamer.

Aspect 4. The conjugate of aspect 3, wherein the aptamer is a DNA aptamer.

Aspect 5. The conjugate of aspect 3, wherein the aptamer is an RNA aptamer.

Aspect 6. The conjugate of aspect 1, wherein the affinity agent is a small molecule.

Aspect 7. The conjugate of aspect 1, wherein the affinity agent is a peptide.

Aspect 8. The conjugate of any one of aspects 1-7, wherein the ligand binds at an allosteric site.

Aspect 9. The conjugate of any one of aspects 1-7, wherein the ligand binds at an orthosteric site.

Aspect 10. The conjugate of any one of aspects 1-9, wherein binding of the ligand to the target ligand-binding polypeptide results in a functional change in the target ligand-binding polypeptide.

Aspect 11. The conjugate of any one of aspects 1-9, wherein binding of the ligand to the target ligand-binding polypeptide results in a conformational change.

Aspect 12. The conjugate of any one of aspects 1-9, wherein binding of the ligand to the target ligand-binding polypeptide results in stabilization of a conformation.

Aspect 13. The conjugate of any one of aspects 1-12, wherein the ligand is an agonist, an antagonist, an allosteric modulator, or a blocker.

Aspect 14. The conjugate of any one of aspects 1-13, wherein the photoisomerizable group comprises a moiety selected from an azobenzene, a fulgide, a spiropyran, a triphenyl methane, a thioindigo, a diarylethene, and an overcrowded alkene.

Aspect 15. The conjugate of any one of aspects 1-13, wherein the photoisomerizable group comprises an azobenzene.

Aspect 16. The conjugate of any one of aspects 1-15, wherein the target ligand-binding polypeptide is selected from a transcription regulator, an ion channel, a cation channel, a ligand-gated ion channel, a voltage-gated ion channel, a quorum sensor, a pheromone receptor, a neurotransmitter receptor, and an enzyme.

Aspect 17. The conjugate of any one of aspects 1-15, wherein the cation channel is a potassium channel, a sodium channel, or a calcium channel.

Aspect 18. The conjugate of any one of aspects 1-15, wherein the ligand-binding polypeptide is a glutamate receptor, a metabotropic glutamate receptor, an ionotropic glutamate receptor, an ionotropic nicotinic acetylcholine receptor, an ionotropic GABA-A receptor, or an ionotropic purinergic P2X receptor.

Aspect 19. The conjugate of aspect 2, wherein the antibody is selected from scFv, sdAb, Fab, Fab', a nanobody, $Fab'_2$, $F(ab')_2$, Fd, Fv, Feb, and SMIP.

Aspect 20. A cell comprising the conjugate of any one of aspects 1-19.

Aspect 20. The cell of aspect 20, wherein the cell is in vitro.

Aspect 22. The cell of aspect 20, wherein the cell is in vivo.

Aspect 23. The cell of any one of aspects 20-22, wherein the cell is a neuronal cell.

Aspect 24. The cell of any one of aspects 20-22, wherein the cell is a retinal cell.

Aspect 25. The cell of any one of aspects 20-22, wherein the cell is a muscle cell.

Aspect 26. A method of modulating activity of a target polypeptide, the method comprising: a) contacting the target polypeptide with the conjugate of any one of aspects 1-19, generating a light-regulatable polypeptide; and b) exposing the light-regulatable polypeptide to light of a wavelength that results in binding of the ligand to the light-regulatable polypeptide, wherein binding of the ligand to the light-regulatable polypeptide modulates activity of the light-regulatable polypeptide.

Aspect 27. The method of aspect 26, wherein the ligand is an agonist, and wherein binding of the ligand to the light-regulatable polypeptide results in activation of the light-regulatable polypeptide.

Aspect 28. The method of aspect 26, wherein the ligand is an antagonist, and wherein binding of the ligand to the light-regulatable polypeptide results in inhibition, desensitization, or inactivation of the light-regulatable polypeptide.

Aspect 29. The method of any one of aspects 26-28, wherein the target polypeptide is selected from a transcription regulator, an ion channel, a cation channel, a ligand-gated ion channel, a voltage-gated ion channel, a quorum sensor, a pheromone receptor, a neurotransmitter receptor, an enzyme, enzyme, a motor protein, a transporter, a membrane transport protein, a G protein-coupled receptor, a G protein, a receptor tyrosine kinase, a scaffolding protein, an adaptor protein, a cytoskeletal protein, an adhesion protein, a membrane-targeting protein, a protein that direct secretion, and a localization or protein interaction domain of a protein.

Aspect 30. The method of any one of aspects 26-28, wherein the cation channel is a potassium channel, a sodium channel, or a calcium channel.

Aspect 31. The method of any one of aspects 26-30, wherein the target polypeptide is in a cell.

Aspect 32. The method of aspect 31, wherein the cell is in vitro.

Aspect 33. The method of aspect 31, wherein the cell is in vivo.

Aspect 34. The method of any one of aspects 31-33, wherein the cell is a retinal cell.

Aspect 35. The method of any one of aspects 31-33, wherein the cell is a neuronal cell.

Aspect 36. The method of any one of aspects 31-33, wherein the cell is a muscle cell.

Aspect 37. A method of modulating activity of a target cell population, the method comprising exposing a target cell population to light, wherein the target cell population comprises the conjugate of any one of aspects 1-19, wherein the light is of a wavelength that results in binding of the ligand to the light-regulatable polypeptide, and wherein binding of the ligand to the light-regulatable polypeptide modulates activity of the target cell population.

Aspect 38. The method of aspect 37, wherein the target cell population is present in a tissue.

Aspect 39. The method of aspect 38, wherein the tissue is in vivo.

Aspect 40. The method of aspect 37, wherein the target cell population is in vivo.

Aspect 41. The method of aspect 37, wherein the target cell population is in vitro.

Aspect 42. The method of any one of aspects 37-41, wherein the target cell population is present in a mixed cell population comprising the target cell population and non-target cells.

Aspect 43. The method of aspect 39, wherein the tissue is brain tissue.

Aspect 44. The method of aspect 39, wherein the tissue is muscle tissue.

Aspect 45. The method of aspect 39, wherein the tissue comprises blood cells.

Aspect 46. A method of increasing the sensitivity of a retinal cell to light, the method comprising exposing the retinal cell to light, wherein the retinal cell comprises the conjugate of any one of aspects 1-19, wherein the light is of a wavelength that results in binding of the ligand to the light-regulatable polypeptide, and wherein binding of the ligand to the light-regulatable polypeptide increases the sensitivity of the retinal cell to light.

Aspect 47. A method of conferring light responsiveness on a retinal cell, the method comprising introducing into the retinal cell the conjugate of any one of aspects 1-19.

Aspect 48. A method of treating an ocular disorder characterized by reduced responsiveness to light, the method comprising administering the conjugate of any one of aspects 1-19 to an eye of an individual having the ocular disorder.

Aspect 49. The method of aspect 48, wherein the ocular disorder is an inherited retinal degenerative disease.

Aspect 50. The method of aspect 49, wherein the disease is retinitis pigmentosa or age-related macular degeneration.

Aspect 51. A method of modulating activity of a target polypeptide, the method comprising: a) contacting a cell comprising the target polypeptide with a photoisomerizable regulator comprising i) a photoisomerizable group; and ii) a ligand that binds to the target ligand-binding polypeptide, wherein the cell is genetically modified with a nucleic acid comprising a nucleotide sequence encoding a fusion polypeptide comprising: i) an affinity agent that specifically binds to an epitope presented by the target polypeptide; and ii) a HALO-tag, a SNAP-tag, or a CLIP-tag, wherein the fusion polypeptide forms a conjugate with the photoisomerizable regulator, and wherein the affinity agent present in the conjugate binds to the target polypeptide, generating a light-regulatable polypeptide; and b) exposing the light-regulatable polypeptide to light of a wavelength that results in binding of the ligand to the light-regulatable polypeptide, and wherein binding of the ligand to the light-regulatable polypeptide modulates activity of the light-regulatable polypeptide.

Aspect 52. The method of aspect 51, wherein the nucleic acid is present in a recombinant expression vector.

Aspect 53. The method of aspect 51, wherein the affinity agent is an antibody.

Aspect 54. The method of aspect 52, wherein the affinity agent is a nanobody or a scFv.

Aspect 55. The method of any one of aspects 51-54, wherein the cell is in vivo.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Generation of Affinity Agent-Photoisomerizable Regulator Conjugates A method for non-genetic delivery of a photoswitch to a target protein has been developed. The approach includes use of an affinity moiety that is specific for the target protein or an associated protein. The affinity moiety can be an antibody, peptide, polynucleotide aptamer or synthetic chemical, where the binding has minimal or no effect on the function of the target protein but brings the photoswitch to it. The following examples demonstrate this method by using a nanobody (NB) as an affinity moiety.

A photoisomerizable regulator was used that includes SNAP-selective benzylguanine (BG) reactive group at one end, a linker of adjustable length, an azobenzene (A) photoisomerizable group, and a glutamate (G) ligand on the distal end (BGAG) (FIG. 1B, C). The gene encoding a SNAP tag domain, to which the BGAG photoswitch attaches, was fused in-frame to the gene encoding a nanobody (NB) to generate a 2-part complex: NB-SNAP to which BGAG could then be attached (FIG. 1D, left and middle). In this example case, a nanobody (NB) that binds green fluorescent protein (GFP) was used, thus enabling a BGAG photoswitch that is attached to the SNAP to be selectively delivered to a GFP-tagged target protein. The target protein was a fusion protein comprising mGluR2 with GFP fused to its N-terminus, just "above" the ligand binding domain (LBD) (FIG. 1D, right). The SNAP-antiGFP NB fusion protein was purified and conjugated in solution to BGAG to generate the 3-part complex: SNAP(BGAG)-NB. The SNAP(BGAG)-NB photoswitch-protein complex was applied to cells expressing GFP-mGluR2. Binding of SNAP (BGAG)-NB to GFP-mGluR2 positions the BGAG in such a way that illumination with 380 nm light isomerizes the BGAG photoswitch to cis and binds the ligand to the LBD (FIG. 1D). This will activate the receptor, whereas 500 nm light will isomerize the BGAG photoswitch back to trans to unbind the ligand and deactivate the receptor.

Figure 2:
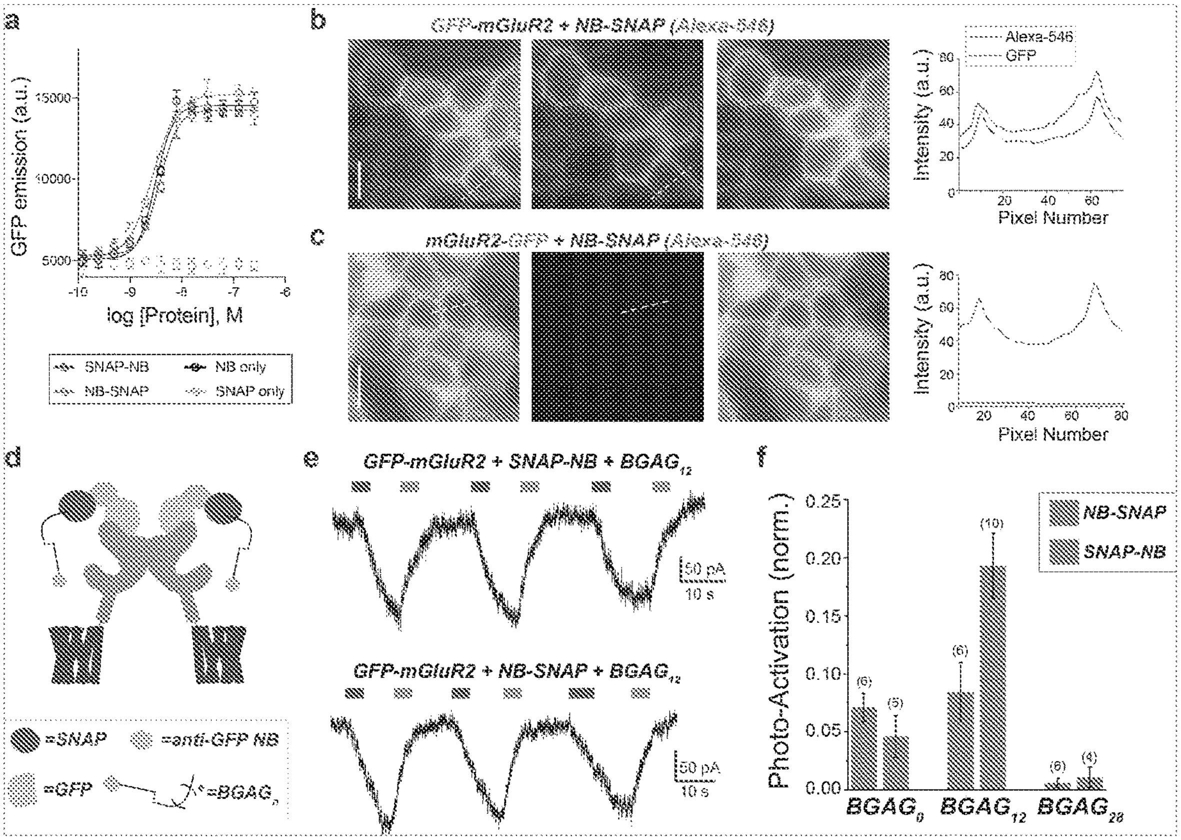
FIG. 2A-2F depict characterization of the use of a SNAP-tagged anti-green fluorescent protein (GFP) nanobody (NB) (SNAP-NB or NB-SNAP) to bring a photoswitch to a GFP-tagged metabotropic glutamate receptor (GFP-mGluR2). (a) shows that GFP binding is not perturbed by attachment of a SNAP-tag to the NB and (b, c) show that purified NB-SNAP is able to efficiently bind GFP-mGluR2 expressed in HEK 293T cells. The schematic in (d) shows the arrangement of the components after association with the GFP-mGluR2 target. (d) shows reproducible and reversible photo-activation of mGluR2 by the BGAG photoswitch that is attached to either SNAP-NB (top) or NB-SNAP (bottom) in HEK 293T cells to activate co-expressed G protein-coupled GIRK channels. (e) and (f) show quantification of the BGAG photoswitch length dependence for both SNAP-NB and NB-SNAP.
Figure 3:
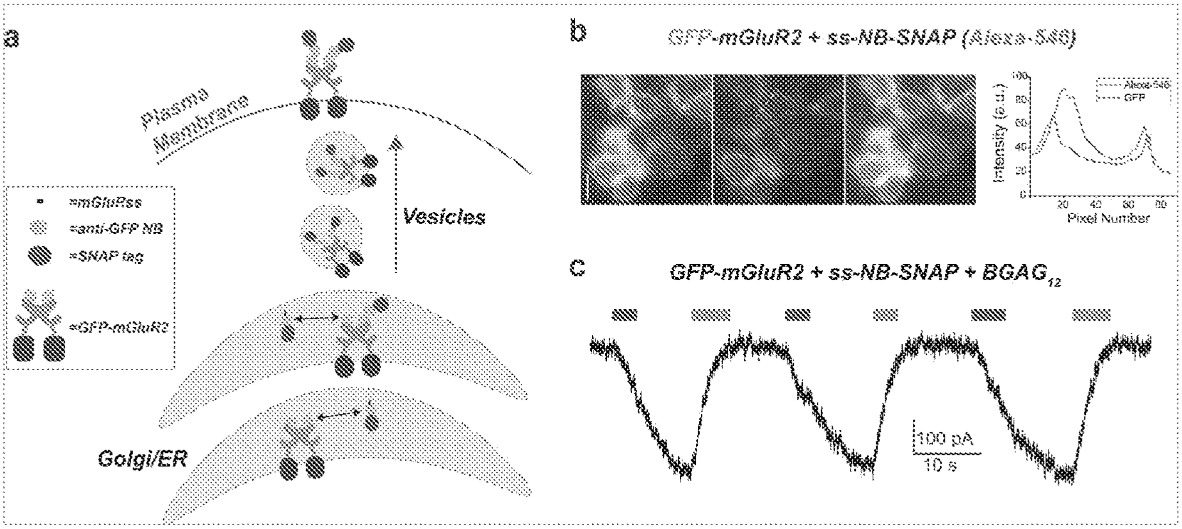
FIG. 3A-3C show that the anti-GFP NB, with an added signal sequence from mGluR (mGluRss) (a), can be co-expressed with GFP-mGluR2 and can co-assemble, as seen from co-localization (b), and elicit strong photo-activation (c).

Binding of the SNAP-NB protein complex to cells expressing GFP-mGluR2 can be gauged by labeling the SNAP with a fluorescent dye that is conjugated to BG. This showed specific binding (FIG. 2A-C). The SNAP(BGAG)-NB bound GFP-mGluR2 or mGluR2-GFP 4-part complex (FIG. 2D) was activated by light, as detected by the activation of GIRK channels by the G■ that is released by the activated mGluR2 (FIG. 2E). Illumination with 380 nm light isomerized the BGAG photoswitch to cis, bound the ligand to the ligand-binding domain (LBD), and activated the receptor and, therefore, the channel. This drove an inward current into the HEK293 cell at the negative holding potential (−60 mV) with high (150 mM) $K^+$ in the bath. Illumination with 500 nm light isomerizes the BGAG photoswitch back to trans, unbinds the ligand from the ligand-binding domain (LBD), deactivated the receptor and so turned off the GIRK current. As expected, the efficacy of photo-activation depends on the length of the linker between the BG and azobenzene (FIG. 2F). The binding of the NB-SNAP or SNAP-NB to the target protein was so stable, that the complex were formed in cells when the NB-SNAP or SNAP-NB was co-expressed with the GFP-tagged mGluR2 and this way also yielded photo-activation once the BGAG photoswitch was applied to the cells (FIG. 3).

Figure 4:
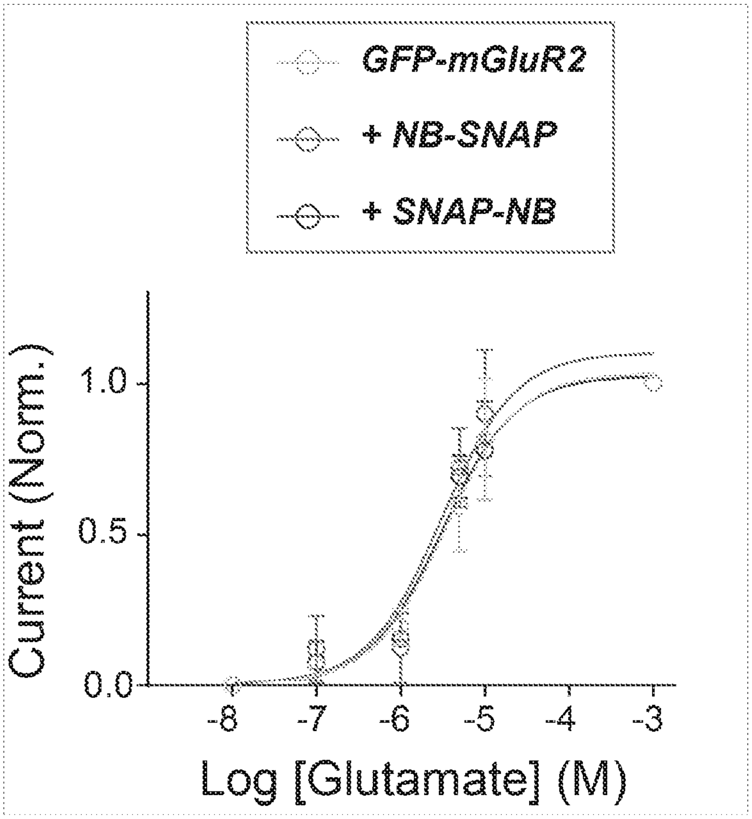
FIG. 4 shows that NB-SNAP or SNAP-NB attachment to GFP-mGluR2 does not alter the apparent glutamate affinity of mGluR2, i.e., the data show lack of perturbation of the target protein's function by the attachment assembly.
Figure 5:
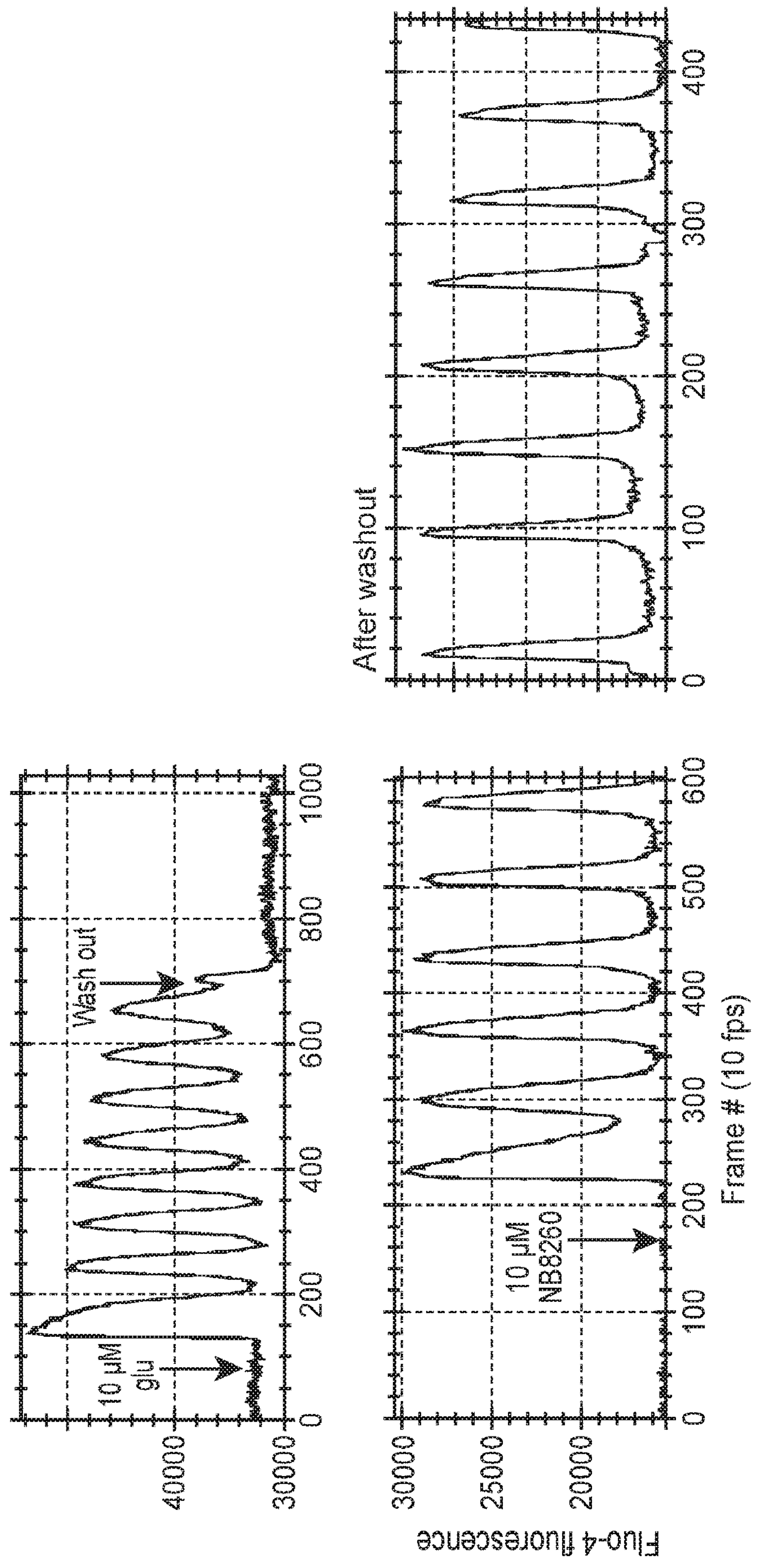
FIG. 5 shows that binding of a nanobody can on its own alter the activity state of a target protein, e.g. NB-8260 binding to the mGluR5 ectodomain (in absence of glutamate) activates the receptor and triggers calcium waves in HEK293 cells. The activation by NB-8260 (bottom) is as potent as that elicited by glutamate (top) and persists much longer after washout because of the tight binding of the NB.
Figure 6:
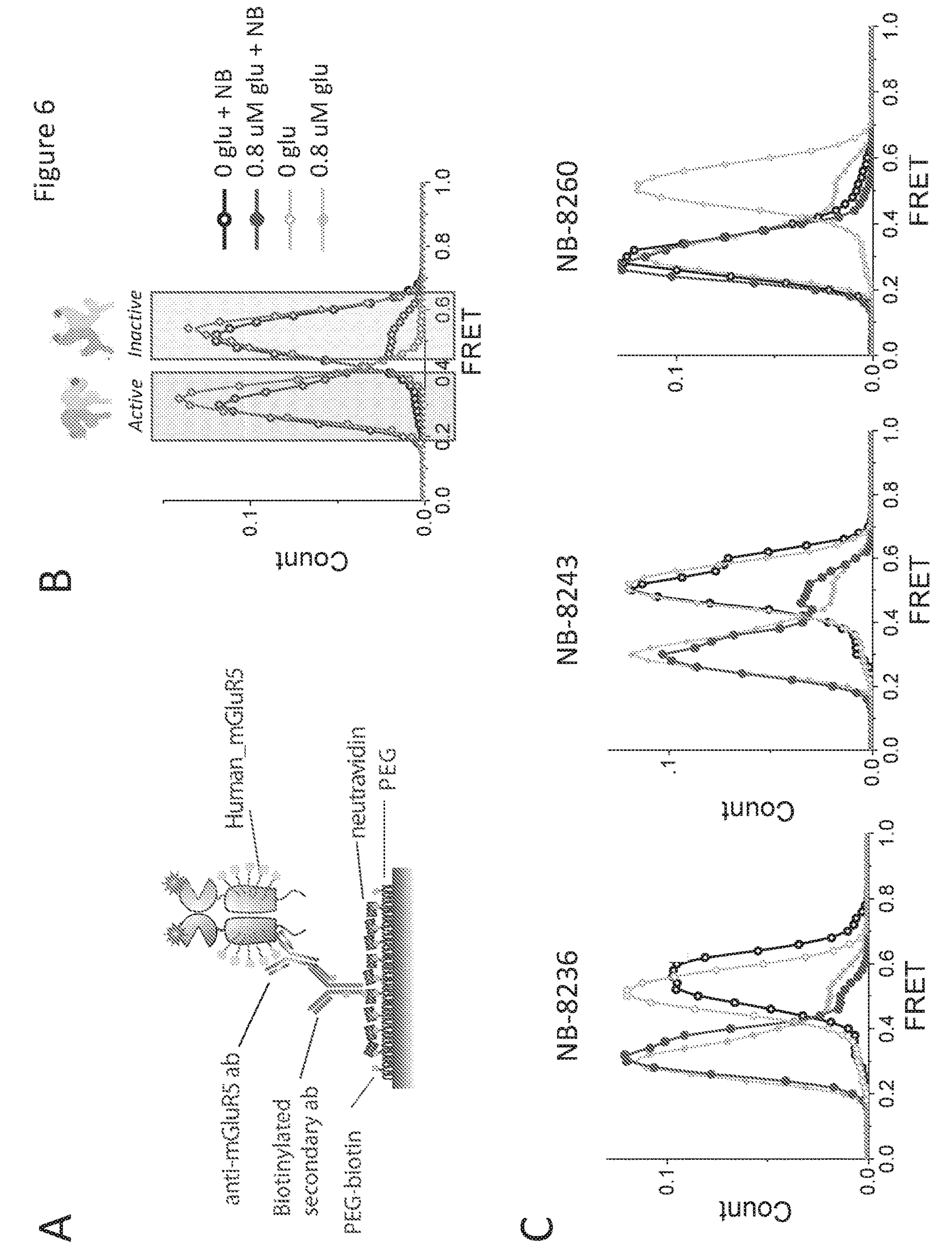
FIG. 6A-6C depicts single molecule analysis of structural rearrangement that underlies activation of mGluR5 homodimers to show that a nanobody (NB) can activate the receptor strongly (NB-8260), weakly (NB-8236) or not at all (NB-8243, SEQ ID NO: 4), indicating that functional analysis can be used to select NBs that will deliver the photoswitch to the protein target without perturbing the target's function.

Because the GFP is a large separate domain that is fused to the mGluR2 target protein, binding of the NB to the GFP does not change the function of mGluR2 (FIG. 4). However, the goal was to target the native, unmodified proteins in cells, tissues or the intact organism, and this would require the affinity moiety to attach directly to the target protein, something that could impact function of the target protein. Affinity moieties whose binding does not alter the function of the target protein would be desirable. This notion was tested by asking whether there would be a functional impact of nanobody binding to an mGluR. For this purpose, mGluR5 was selected. mGluR5 is a Gq-coupled receptor whose activation stimulates phospholipase C to generate IP3 and trigger the release of calcium from internal stores, which could detect with the calcium indicator FLUO-4 that was loaded into the cells in its AM ester form. It was found that, just as glutamate activates calcium waves in HEK293 cells expressing mGluR5 (FIG. 5, top), so too an anti-mGluR5 nanobody, NB-8260, also activated calcium waves (FIG. 5, bottom). Because of the high affinity of NB-8260, the waves persisted much longer after washout of excess NB-8260 from the bath (FIG. 5, bottom) than after washout of glutamate (FIG. 5, top). The activation of the receptor by NB-8260 could be directly detected using single molecule fluorescence resonance energy transfer (smFRET). SNAP-mGluR5 dimers labeled in HEK293 cells with a mixture of FRET donor and acceptor (green and red) BG dyes were isolated by cell lysis and immune-purified and immobilized at low density on a passivated glass surface (FIG. 6A) for total internal reflection fluorescence (TRIF) microscopy. Individual spots containing both the green and red dye (i.e. one on each subunit of the dimer) were selected for analysis and FRET levels measured: i) in the absence of ligand; ii) in 0.8 mM glutamate; iii) in the presence of a nanobody; or iv) in a combination of 0.8 mM glutamate and the nanobody. In the absence of activating ligand, the receptors adopt an "open" conformation of the LBD, which places the donor and acceptor in relatively close proximity, yielding a "high" FRET level of ~0.5 (FIG. 6B). When activated by glutamate the LBDs close and move the dyes further apart, yielding the low FRET state of ~0.3 (FIG. 6B). As can be seen in FIG. 6C, NB-8260 was as potent an activator as glutamate, whereas NB-8236 activated weakly and NB-8243 (SEQ ID NO: 4) did not activate at all. Thus, NB-8243 (SEQ ID NO: 4) can be used as a non-perturbing affinity moiety to bring the photoswitch to the unmodified, native mGluR5.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A conjugate comprising:

a) an affinity agent that specifically binds to a metabotropic glutamate receptor, wherein the affinity agent is a nanobody comprising the sequence of SEQ ID NO: 4;

b) a linker; and c) a photoisomerizable regulator comprising:

i) a photoisomerizable group, wherein the photoisomerizable group comprises an azobenzene; and ii) a ligand that binds to the metabotropic glutamate receptor, wherein the ligand is a D stereoisomer, wherein the conjugate is configured to attach to the metabotropic glutamate receptor solely via binding of the affinity agent to the metabotropic glutamate receptor.

2. The conjugate of claim 1, wherein the ligand binds at an allosteric site or at an orthosteric site.

3. The conjugate of claim 1, wherein the ligand is an agonist, an antagonist, an allosteric modulator, or a blocker.

4. A cell comprising the conjugate of claim 1.

5. The cell of claim 4, wherein the cell is in vitro.

6. The cell of claim 4, wherein the cell is in vivo.

7. The cell of claim 4, wherein the cell is a neuronal cell.

8. The cell of claim 4, wherein the cell is a retinal cell.

9. The cell of claim 4, wherein the cell is a muscle cell.

* * * * *

```
                              SEQUENCE LISTING


<160> NUMBER OF SEQ ID NOS: 4

<210> SEQ ID NO 1
<211> LENGTH: 182
<212> TYPE: PRT
<213> ORGANISM: Artificial sequence
<220> FEATURE:
<223> OTHER INFORMATION: Synthetic polypeptide

<400> SEQUENCE: 1

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Ser His Leu Ala Ala Leu Ala Gly Asn Pro Ala Ala Thr Ala
        115                 120                 125

Ala Val Lys Thr Ala Leu Ser Gly Asn Pro Val Pro Ile Leu Ile Pro
    130                 135                 140

Cys His Arg Val Val Gln Gly Asp Leu Asp Val Gly Gly Tyr Glu Gly
145                 150                 155                 160
```

-continued

```
Gly Leu Ala Val Lys Glu Trp Leu Leu Ala His Glu Gly His Arg Leu
                165                 170                 175

Gly Lys Pro Gly Leu Gly
            180


<210> SEQ ID NO 2
<211> LENGTH: 297
<212> TYPE: PRT
<213> ORGANISM: Artificial sequence
<220> FEATURE:
<223> OTHER INFORMATION: Synthetic polypeptide

<400> SEQUENCE: 2

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295


<210> SEQ ID NO 3
<211> LENGTH: 182
<212> TYPE: PRT
<213> ORGANISM: Artificial sequence
<220> FEATURE:
```

<223> OTHER INFORMATION: Synthetic polypeptide

<400> SEQUENCE: 3

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
            20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Ile Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Glu Ser His Leu Ala Ala Leu Val Gly Asn Pro Ala Ala Thr Ala
        115                 120                 125

Ala Val Asn Thr Ala Leu Asp Gly Asn Pro Val Pro Ile Leu Ile Pro
    130                 135                 140

Cys His Arg Val Val Gln Gly Asp Ser Asp Val Gly Pro Tyr Leu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 4
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 4

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Ser Tyr
            20                  25                  30

Ala Met Gly Trp Phe Arg Gln Ala Pro Gly Lys Glu Arg Glu Ser Val
        35                  40                  45

Ala Ala Ile Ser Ser Ser Gly Gly Ser Thr His Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Met Tyr Gly Ser Arg Trp Pro Asp Trp Glu Tyr Asp Tyr
            100                 105                 110

Trp Gly Gln Gly Thr Gln Val Thr Val Ser Ser
        115                 120